US010577663B2

(12) United States Patent
Moen et al.

(10) Patent No.: US 10,577,663 B2
(45) Date of Patent: Mar. 3, 2020

(54) PREDICTING RESISTANCE TO VIRAL INFECTION

(71) Applicant: AquaGen AS, Trondheim (NO)

(72) Inventors: Thomas Moen, Aas (NO); Jacob Seilo Torgersen, Aas (NO); Nina K. Santi, Trondheim (NO)

(73) Assignee: Aqua Gen AS, Trondheim (NO)

(*) Notice: Subject to any disclaimer, the term of this patent is extended or adjusted under 35 U.S.C. 154(b) by 3 days.

(21) Appl. No.: 15/102,979

(22) PCT Filed: Jan. 8, 2015

(86) PCT No.: PCT/GB2015/050030
§ 371 (c)(1),
(2) Date: Jun. 9, 2016

(87) PCT Pub. No.: WO2015/104550
PCT Pub. Date: Jul. 16, 2015

(65) Prior Publication Data
US 2016/0304974 A1 Oct. 20, 2016

(30) Foreign Application Priority Data

Jan. 8, 2014 (GB) .................................. 1400309.9

(51) Int. Cl.
C12Q 1/6888 (2018.01)
A61K 38/17 (2006.01)
A61K 48/00 (2006.01)

(52) U.S. Cl.
CPC .......... *C12Q 1/6888* (2013.01); *A61K 38/177* (2013.01); *A61K 48/00* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS 9,920,368 B2 * 3/2018 Moen .................. C12Q 1/6874

FOREIGN PATENT DOCUMENTS

WO 2006/047673 A2 5/2006
WO 2007084488 A2 7/2007
WO 2014/006428 A1 1/2014

OTHER PUBLICATIONS

Hirschhorn et al. Genetics in Medicine. vol. 4, No. 2, pp. 45-61, Mar. 2002.*
Lucentini et al The Scientist (2004) vol. 18, p. 20.*
Langdahl et al Journal of Bone and Mineral Research (2000) 15: 402-414.*
Li et al BMC Genetics. 2010. 11:47.*
Gagneux (Molecular Phylogenetics and Evolution. 2001. 18: 2-13.*
Halushka (Nature. Jul. 1999. 22: 239-247.*
Mummidi et al Journal of Biological Chemistry 2000 vol. 275 No. 25 pp. 18946-18961.*
Leong et al BMC Genomics. 2010. 11: 279, pp. 1-17 (Year: 2010).*
NCBI Database GenBank Accession No. BT058864.1, Aug. 24, 2010 (Year: 2010).*
GenBank DR696409.1. National Center for Biotechnology Informaiton. NCBI Database, National Library of Medicine, Jul. 13, 2005, available via URL: <ncbi.nlm.nih.gov/nuccore/DR696409.1/>.*
R. D. Houston et al. "Major Quantitative Trait Loci Affect Resistance to Infectious Pancreatic Necrosis in Atlantic Salmon (*Salmo salar*)", Genetics, vol. 178, No. 2, Feb. 1, 2008 (Feb. 1, 2008), pp. 1109-1115.
C. Cofre et al. "Phenotype gene expression differences between resistant and susceptible salmon families to IPNV", Fish Physiology and Biochemistry, vol. 40, No. 3, Dec. 4, 2013 (Dec. 4, 2013), pp. 887-896.
Zazula Monika et al. "CDH1 gene promoter hypermethylation in gastric cancer: relationship to Goseki grading, microsatellite instability status, and EBV invasion" Diagnostic Molecular Pathology: The American Journal of Surgical Pathology, Part B, Mar. 2006, vol. 15, No. 1, Mar. 2006, pp. 24-29.
Baigil'Dina A. A., et al. "Genetic determining of the change in VE-cadherin expression and intensified vessel deendothelisation during hemorrhagic fever with renal syndrome", Molecular Genetics, Microbiology and Virology, Allerton Prees, Inc., Heidelberg, vol. 27, No. 4, Dec. 28, 2012 (Dec. 28, 2012), pp. 160-166.
K. Tran et al.: "Inactivation and Disassembly of the Anaphase-Promoting Complex during Human Cytomegalovirus Infection is Associated with Degradation of the APC5 and APC 4 Subunits and Does Not Require UL97-Mediated Phosphorylation of Cdh1", Journal of Virology, vol. 84, No. 20, Oct. 15, 2010 (Oct. 15, 2010), pp. 10832-10843.
International Search Report for PCT/GB2015/050030 dated Mar. 27, 2015, 4 pgs.
Granzow H, Weiland F, Fichtner D and Enzmann PJ (1997) Studies of the ultrastructure and morphogenesis of fish pathogenic viruses grown in cell culture. Journal of Fish Diseases 20: 1-10.
Falk K, Namork E, Dannevig BH (1998) Characterization and applications of a monoclonal antibody against infectious salmon anaemia virus. Dis Aquat Organ 8: 77-85.
Houston RD, Haley CS, Hamilton A, Guy DR, Tinch AE, Taggart JB, McAndrew BJ, Bishop SC (2008) Major quantitative trait loci affect resistance to infectious pancreatic necrosis in Atlantic salmon (*Salmo salar*). Genetics 178: 1109-15.
Houston RD, Davey JW, Bishop SC, Lowe, NR, Mota-Velasco JC et al. (2012) Characterisation of QTL-linked and genome-wide restriction site-associated DNA (RAD) markers in farmed Atlantic salmon. BMC Genomics 13: 244.

(Continued)

Primary Examiner — Carla J Myers
(74) Attorney, Agent, or Firm — Praedcere Law

(57) ABSTRACT

The present invention relates to a method of predicting resistance to a viral infection in a subject, the method comprising determining in the subject the variant present at one or more amino acid position in a cadherin protein, and/or the alleles present at one or more DNA polymorphism in the gene for cadherin, and predicting whether or not the subject is resistant to viral infection based on the determination of the variant and/or the alleles.

4 Claims, 9 Drawing Sheets
Specification includes a Sequence Listing.

(56) References Cited

OTHER PUBLICATIONS

Kuznar J, Soller M, Fabias G, Espinoza JC (1995) Attachment and entry of infectious pancreatic necrosis virus (IPNV) into CHSE-214 cells. Arch Virol 140: 1833-40.

Lien S, Gidskehaug L, Moen T, Hayes BJ, Berg PR, Davidson WS, Omholt SW, Kent MP (2011) A dense SNP-based linkage map for Atlantic salmon (*Salmo salar*) reveals extended chromosome homeologies and striking differences in sex-specific recombination patterns. BMC Genomics 12: 615.

Madsen and Jensen (2008) DMU: a user's guide. A package for analysing multivariate mixed models, version 6, release 5.0. University of Aarhus, Tjele, Denmark.

McLoughlin MF, Graham DA (2007). Alphavirus infections in salmonids—a review. J. Fish Dis. 30: 511-531.

Moen T, Hayes B, Baranski M, Berg PR, Kjøglum S, Koop BF, Davidson WS, Omholt SW, Lien S (2008) A linkage—map of the Atlantic salmon (*Salmo salar*) based on EST-derived SNP markers. BMC Genomics 9: 223.

Moen T, Baranski M, Sonesson AK, Kjøglum S (2009) Confirmation and fine-mapping of a major QTL for resistance to infectious pancreatic necrosis in Atlantic salmon (*Salmo salar*): population-level associations between markers and trait. BMC Genomics 10: 368.

Palacios G, Lovoll M, Tengs T, Hornig M, Hutchison S et al. (2010) Heart and Skeletal Muscle Inflammation of Farmed Salmon is Associated with Infection with a Novel Reovirus. PLoS ONE 5: e11487.

Shifman S, Kuypers J, Kokoris M, Yakir B, Darvasi A (2003) Linkage diseuilibrium patterns of the human genome across populations. Human Molecular Genetics 12: 771-776.

Thorsen J, Zhu B, Frengen E, Osoegawa K, de Jong, PJ, Koop BF, Davidson WS, Høyheim B (2005) A highly redundant BAC library of Atlantic salmon (*Salmo salar*): an important tool for salmon projects. BMC Genomics 6: 50.

Yoon M, Spear PG (2002). Disruption of adherens junctions liberates nectin-1 to serve as receptor for herpes simplex virus and pseudorabies virus entry. J Virol. 76:7203-8.

Lopes et al, "1Alpha,25-hydroxyvitamin D3, Induces de novo E-cadherin Expression in Triple-negative Breast Cancer Cells by CDH1-promoter Demethylation", Anticancer Research 32, 2012, pp. 249-258.

Liu et al, "Loss of CDH1 up-regulates epidermal growth factor receptor via phosphorylation of YBX1 in non-small cell lung cancer cells", FEBS Letters 587, 2013, pp. 3995-4000.

Arzumanyan et al, "Epigenetic repression of E-cadherin expression by hepatitis B virus x antigen in liver cancer", Oncogene 31, 2012, pp. 563-572.

Brasch et al, "Thinking outside the cell: how cadherins drive adhesion", Trends in Cell Biology vol. 22, Jun. 2012, pp. 299-310.

\* cited by examiner

PREDICTING RESISTANCE TO VIRAL INFECTION

REFERENCE TO A "SEQUENCE LISTING," A TABLE, OR A COMPUTER PROGRAM LISTING APPENDIX SUBMITTED AS AN ASCII TEXT FILE

The material in the substitute ASCII text file named MURG-60008-SeqLst-amended.txt," created Sep. 16, 2019, file size of 6.45 KB, is hereby incorporated by reference.

The present invention relates to methods for predicting resistance to viral infection and to methods for preventing and treating viral infection.

Viruses (and virions, being the virus particles) are non-cellular infective agents that are capable of reproducing in animal host cells. A virus includes a nucleic acid (either DNA or RNA) at its core, surrounded by a proteinaceous capsid (and in some cases an outer envelope). Epithelial barriers are the main point of entry for viruses into the body. The host cells impose multiple barriers to virus entry, and virus entry pathways are largely defined by the interactions between virus particles and their receptors at the cell surface. After entry, the virus replicate inside the host cell by interacting with the host cells' replicative and protein-producing apparatus and in so doing direct the host cell to produce virions, which are released from the host cell upon its lysis or by budding of the cell membrane. Viruses are the causative agent in a number of human and animal infections, such as influenza, measles, hepatitis, rabies, foot-and-mouth disease, infectious bursal disease (IBDV), infectious pancreatic necrosis (IPN), pancreas disease (PD), heart and skeletal muscle inflammation (HSMI), infectious salmon anaemia (ISA) and cardiomyopathy syndrome (CMS).

Treatments that have been found for some viral infections are based on the use of vaccines or anti-viral therapeutics (prophylactically or otherwise). Vaccines recruit the subject's own immune responses to fight viral infection, but may not be effective if the subject's immune response is not receptive to the vaccine or can induce inappropriate immune responses that may be damaging to the subject. Anti-viral therapeutics achieve their effect in a number of potential ways (predominantly by preventing viral synthesis such as is the case for acyclovir), but resistance in virus populations to these therapeutics is known.

Apart from the obvious damage caused by viruses to the human and non-human animal population, viral infections pose a severe economic threat to many agri- and aquacultural industries. For example, infectious pancreatic necrosis (IPN) is one of the major threats to the fish farming industry worldwide. The disease is caused by an aquatic birnavirus, causing necrosis of pancreatic cells and liver cells, resulting in lethargy and sudden mortality. The virus is wide-spread in nature, but does not seem to affect free-living salmon to any large extent. In aquaculture environments, the disease causes mortalities both at the fry stage, when the fish are still living in fresh water, and at the post-smolt stage, shortly after transfer to sea water. The industry-wide losses in salmon farming due to IPN have been estimated to be 8% during the fresh water phase and 5% during the sea phase. The IPN virus genome consists of two genomic segment (A and B), encoding four (VP2-VP5) and one (VP1) viral proteins, respectively. Cellular uptake of IPN virus depends upon recognition or a receptor protein, most likely through binding of the capsid protein VP2 to its receptor, followed by endocytosis (Granzow et al. 1997).

Infectious Bursal Disease (also known as IBD or Gumboro Disease) is a highly contagious disease infecting chickens and caused by infectious Bursal Disease virus (IBDV). IBDV can infect chickens, turkeys, ducks, geese and guinea fowl but only chickens show clinical signs of the disease. Infections in chickens with IBDV usually results in mortality at 3 to 6 weeks of age.

Pancreas disease (PD) is another viral disease of importance to the salmon industry. The responsible viral agent, salmonid alphavirus (SAV), infects farmed Atlantic salmon and rainbow trout, and clinical signs are lethargy and sudden inappetence, reduced growth and increased mortality during on-growth in seawater. Similar to IPN, the disease is characterized by necrosis of the exocrine pancreas, but also accompanied by severe cardiac and skeletal muscle lesions. Mortality rates vary from 0 to 50%, and up to 15% of survivors may fail to grow and become runts.

Heart and skeletal muscle inflammation (HSMI) is characterized by severe cardiac and skeletal muscle inflammation of some similarity to PD. The disease is associated with an infection by a piscine reovirus. (Palacios et al. 2010), and typically appears 5 to 9 months after fish are transferred from fresh water to seawater net pens. In severe cases the mortality may reach 20%.

The genetic make-up of the host has a major influence on its response to pathogens and a proportion of subjects may possess natural resistance to viral infection. In the agri- and aquacultural industries there is therefore an advantage in identifying those resistant subjects so that they can be the subject of breeding programs. Additionally, in situations where people are required to be mobilised to areas where viral infection is prevalent and where there are limited medical treatment centres, it can be an advantage to select people that possess natural resistance to the prevalent viral infection. Furthermore, subjects identified as having resistance may be identified as suitable for alternative or no treatment (compared to normal susceptible subjects) with respect to the administration of antiviral drugs or vaccines. By reducing or eliminating treatment of such resistant subjects with antiviral drugs or vaccines, risk associated with such treatments may be reduced.

Detecting resistant subjects is particularly important when attempting to address viral infections for which there is no current treatment. For example, fish breeding companies run continuous fish selection programs aimed at improving the aquaculture stocks with regards to disease resistance and protocols have been developed for testing of fish's resistance to several specific diseases. These challenge tests have been used in order to select fish as broodstock that possess above-average resistance to the diseases in question. Conventional tests involve controlled challenge-testing of siblings of the breeding candidates. This methodology is, however, impeded by the fact that infected fish cannot be used as broodstock. One therefore has to resort to selecting random (un-tested) animals from among the siblings of the tested fish that performed best in the challenge tests (so-called family selection). Single Nucleotide Polymorphisms (SNPs) and other DNA polymorphisms that are associated with resistance to certain viruses have previously been identified. Although these SNPs provide a degree of accuracy in determining, without having to sacrifice the subject, if a subject is likely to be resistant to viral infection, very few SNPs or other types of polymorphisms have been identified that are directly associated with viral resistance (e.g. mutations in the CCR5 gene has been demonstrated to provide resistance to HIV), i.e. very few SNPs or polymorphism have been identified as the causal mutation in providing viral resistance to viral disease. No polymorphisms have been identified to-date that are directly associated with viral infections in lower vertebrates, such as fish, up until the identification of the polymorphisms of the present invention.

There is, since treatments for viral infections are often lacking and often suboptimal, a need for treatments for currently untreatable viral infections and a need for alternative treatments for viral infections for which the aforementioned treatments are currently available. There is also a need for alternative methodologies for assaying animals' resistance to viral infections; particularly methodologies that allow direct assaying of individual's resistance to a viral infection without the killing of the individual (thereby enabling the use of the tested animal as broodstock and the creation of an appropriate method for testing the human population).

The inventor of the present invention has, following extensive experimentation, surprisingly found that polymorphisms in a cadherin gene (ie genes that encode cadherin proteins) and variants in the amino acid sequence of the corresponding cadherin proteins (ie the protein products of cadherin genes) are associated with resistance or susceptibility to viral infection in subjects. These findings lead directly to the understanding of how one may determine the susceptibility status of a subject either through the determination of the gene variants (alleles) carried by the subject at the cadherin genes, or through the determination of the variants in the amino acid sequence of cadherin proteins expressed by the subject. Also, the findings lead directly to the idea that susceptible subjects may be rendered resistant through the administration of vectors that deliver the resistance variant of a cadherin gene to the subject (eg gene therapy).

To-date, there has been no suggestion of a link between cadherin proteins or the genes encoding cadherin proteins and viral resistance, or between these genes/proteins and the treatment of viral infection. Consequently, it is surprising that variants of cadherin proteins and polymorphisms of the cadherin genes are linked to susceptibility or resistance to viral infection.

Accordingly, in a first aspect of the present invention, there is provided a method of predicting resistance to a viral infection in a subject, the method comprising determining in the subject: —(i) the variant present at one or more amino acid position in cadherin protein, and/or the alleles present at one or more DNA polymorphism in the cadherin gene, and predicting whether or not the subject is resistant to viral infection based on the determination of the variant and/or the alleles.

Cadherins are ubiquitous transmembrane proteins that mediate the formation of calcium dependent cell-cell junctions between polarized epithelial cells, and they are characterized by a long extracellular transmembrane domain and a cytoplasmic domain. Cadherins imparts strong cell-to-cell adhesion by bringing two plasma membranes physically together, thereby permitting other junctional complexes to assemble (including tight junctions and desmosomes). Cadherins must dimerise in order to form such junctions. The family of cadherins include N-cadherin (neuronal cadherin or Cdh2), E-cadherin (epithelial cadherin or Cdh-1), P-cadherin (placental cadherin or Cdh3), R-Cadherin (retinal cadherin or Cdh4), Cdh5, K-cadherin (kidney cadherin or Cdh6), Cdh7, Cdh8, Cdh9, Cdh10, Cdh11, Cdh12, Cdh12P2, Cdh13, Cdh14, Cdh15, Cdh16, Cdh17, Cdh18, Cdh19, Cdh20, Cdh22, Cdh24, Cdh26, CELSR1, CELSR2, CELSR3, DSC1, DSC2, DSC3, DSG1, DSG2, DSG3, DSG4. As the skilled person would be aware, CELSR relates to EGF LAG seven-pass G-type receptor, DSC relates to desmocolin, and DSG relates to desmoglein. The members of the cadherin family are highly related and have been shown to provide successful cell-cell adhesion through the formation of homo- and hetero-dimers (ie dimers formed from more than one member of the cadherin family). The polymorphisms and variants of the present invention are thought to be associated with domains in the gene/protein that are responsible for dimerization, and would therefore be expected to have relevance to all member so the cadherin family. The present invention may therefore involve the analysis of the variant or polymorphism associated with any member of the cadherin family.

Consequently, for example, the cadherin of the present invention may be any one or more of: —N-cadherin (neuronal cadherin or Cdh2), E-cadherin (epithelial cadherin or Cdh-1), P-cadherin (placental cadherin or Cdh3), R-Cadherin (retinal cadherin or Cdh4), Cdh5, K-cadherin (kidney cadherin or Cdh6), Cdh7, Cdh8, Cdh9, Cdh10, Cdh11, Cdh12, Cdh12P2, Cdh13, Cdh14, Cdh15, Cdh16, Cdh17, Cdh18, Cdh19, Cdh20, Cdh22, Cdh24, Cdh26, CELSR1, CELSR2, CELSR3, DSC1, DSC2, DSC3, DSG1, DSC2, DSC3, DSG4, or any combination thereof. Each of the aforementioned cadherins may be contemplated individually as part of the present invention. For example, the cadherin could be Cdh-1.

The DNA polymorphism of the present invention may be any polymorphism in the cadherin gene that can confer susceptibility to viral infection in a subject depending on the allele of the polymorphism present in the subject. The variant of the present invention may be any variant at one or more amino acid position in the cadherin protein that can confer susceptibility to viral infection in a subject depending on the presence or absence of that variant in the subject. Polymorphisms of the present invention have been found in domains of cadherin that are associated with dimerization of the cadherin, that are in the extracellular domain, and that are in a cadherin tandem repeat domain (ie tandem repeat domains are known to be present in the extracellular domain of cadherins and are thought to mediate cell-cell contact when bound to calcium).

Consequently, the variant of the present invention may be found in a domain of the cadherin protein that is associated with dimerization of cadherin. The polymorphism of the present invention may be found in the nucleic acid sequence that encodes for that domain.

The variant of the present invention may be found in an extracellular domain of the cadherin protein. The polymorphism of the present invention may be found in the nucleic acid sequence that encodes for that domain.

The variant of the present invention may be found in the cadherin tandem repeat domain of the cadherin protein. The polymorphism of the present invention may be found in the nucleic acid sequence that encodes for that domain. As an example, Table 1 provides an overview of the positions of the cadherin tandem domains in a number of cdh1 orthologs.

TABLE 1

Location of Cadherin tandem repeat domains (CTRD) within some Cdh1 orthologs. ND = Not determined (the fifth cadherin tandem repeat domain is absent or its sequence is too different from the consensus CTRD sequence to be detected).

| Species | Sequence identifier of gene* | CTRD 1 | CTRD 2 | CTRD 3 | CTRD 4 | CTRD 5 |
|---|---|---|---|---|---|---|
| Atlantic salmon | BT058864.1 | 163-263 | 271-375 | 383-487 | 501-595 | ND |
| Human | NM_004360.3 | 158-258 | 266-356 | 379-458 | 492-591 | 598-686 |
| Chicken | NM_001039258.2 | 164-264 | 272-377 | 386-489 | 499-597 | 604-690 |
| Pig | NM_001163060.1 | 158-258 | 266-371 | 379-458 | 492-591 | 604-686 |
| Cattle | AY508164.1 | 158-258 | 266-371 | 379-482 | 492-591 | 604-686 |

*All sequences are referred to by their Genbank VERSION identifiers. The identifiers given in the table pertain to NCBI-GenBank Flat File Release 205.0.

The DNA polymorphisms may also be any DNA polymorphisms that leads to differences in expression levels of a cadherin gene, or any DNA polymorphisms that causes differential splicing of the transcript of a cadherin gene.

The nature of cadherins means that they are found in many animals, and in each animal cadherins perform the same role of forming cell-cell adhesions. The utility of the present invention therefore naturally extends to predicting resistance to viral infection in any subject that includes endogenous cadherin. Consequently, when referring to the cadherin the reference relates to the protein product of the cadherin ortholog found in the subject that is subjected to the method of the present invention. When referring to the cadherin gene the reference relates to the cadherin ortholog found in the subject that is subjected to the method of the present invention. A non-exhaustive list of potential animal subjects is as follows: —human, cow, pig, crustacean, fish or poultry. If the subject is poultry, the poultry may, for example, be a chicken or turkey. If the subject is a fish, the fish may, for example, be cod, a member of the tilapia species, a member of the carp species, zebra fish, an Atlantic salmon (i.e. *Salmo salar*), Pacific Salmon, trout (for example, a rainbow trout (*Oncorhynchus mykiss*)), or another species belonging to the family Salmonidae. If the subject is a crustacean, the subject may be a member of the shrimp species.

Establishing the corresponding domains in which the polymorphisms of the present invention are found in any given animal is well within the ordinary abilities of the person skilled in the art. From a known domain in any given animal, one can identify corresponding domains in other animals. Taking the Cdh-1 as an example, one can carry out multiple alignment analysis of nucleic acids encoding, or amino acid sequences for, that protein (using, for example, Clustal Omega analysis). See FIG. 1A and FIG. 1B as an example.

The inventor has found that for diploid organisms the DNA polymorphisms of the present invention can be present in either of two forms, i.e. each of the polymorphisms has two alleles. One allele can be characterised as being predictive of resistance to viral infection (i.e. the resistance allele); the other being predictive of non-resistance to viral infection (i.e. non-resistance allele). The majority of animals are diploid organisms, and thus possess two copies of DNA polymorphisms such as the polymorphisms of the present invention (one copy to be found in each set of chromosomes). However, it is important to note that the invention extends to methods applied to polyploidy organisms (such as triploid fish); the skilled person would be aware how to extend the teachings of the present invention to such organisms where, for example with triploid organisms, three copies of the polymorphisms will exist within the subject. The step of determining the alleles in the method of the first aspect of the present invention may therefore include the step of analysing the DNA polymorphisms provided in each set of chromosomes in order to determine whether each copy of the DNA polymorphism present is a resistance allele or a non-resistance allele. When, for a diploid organism, a subject is subjected to the method of the present invention and is determined to have two copies of the resistance allele for the DNA polymorphism (i.e. the subject is homozygous for the resistance allele), the subject is predicted to have resistance to viral infection. Conversely, when a subject that is subjected to the method of the present invention is determined to have two copies of the non-resistance allele for the DNA polymorphism (i.e. is homozygous for the non-resistance allele), the subject is predicted not to have resistance to viral infection (ie to be more susceptible to viral infection than the subject matter that is homozygous for the resistance allele). It should be noted that the Atlantic salmon, and other species within the Salmoninae subfamily, are so-called pseudo-tetraploid species. One consequence of this pseudo-tetraploid state is that in these species, genes will, to a larger extent than in humans and other non-pseudo-tetraploid species, be duplicated within the genome. A duplicated gene occurs in two or more copies within the genome. In a pseudo-tetraploid species, the copies of the duplicated gene will tend to have slightly different nucleotide sequences, and they will tend to serve slightly different biological roles. Furthermore, in a pseudo-tetraploid species, the inheritance pattern of each copy of a duplicated gene will normally be disomic (as opposed to tetrasomic). Therefore, within the context of this application, pseudo-tetraploid species will be treated as diploid species.

It may be concluded that a subject that is predicted by the method of the present invention as having resistance to viral infection has a greater than normal chance of having resistance to viral infection. Conversely, it may be concluded that a subject that is predicted not to have resistance to viral infection has a lower than normal risk of developing viral infection. When a subject subjected to the method of the present invention is determined to have one copy of the resistance allele for the DNA polymorphism and one copy of the non-resistance allele for the DNA polymorphism (i.e. is heterozygous), the subject would not be predicted according to the present invention to have resistance to viral infection. However, that subject would be predicted to have a greater chance of being resistant to viral infection than a subject with two copies of the non-resistance allele. Henceforth, such as subject will be referred to as having semi-resistance to the viral infection.

Not wishing to be restricted further, but in the interests of clarity, taking Cdh-1 as an example of a cadherin of the present invention, further details of polymorphisms and variants according to the present invention are discussed below.

Consequently, the methods of the present invention may include the determining in the subject of the variant present at one or more amino acid position in Cdh-1, and/or the alleles present at one or more DNA polymorphism in the gene for Cdh-1 (cdh1), and predicting whether or not the subject is resistant to viral infection based on the determination of the variant and/or the alleles.

Cdh1 proteins are also known by the terms E-cadherin, epithelial cadherin, uvomorulin, CD324, CAM 120/180 or Cadherin-1; but are referred to hereinafter as Cdh1. Nomenclature for abbreviated gene names differ between species; here we have adopted the nomenclature used in zebrafish, where gene names are written in lower case italics (e.g. cdh1) and protein names are written with one capital letter (Cdh1). This nomenclature will be used throughout, irrespective of the species (ie irrespective of the fact that, for example, the human orthologs of chd1 and Cdh1 are CDH1 and CDH1).

The extracellular region of Cdh1 is known to be involved in intercellular and intracellular homeotypic interactions and clustering, whereas its cytoplasmic tail is known to associate with an array of intracellular proteins, including beta-catenin, which mediates indirect binding of Cdh1 to the cytoskeleton. The binding of Cdh1 to beta-catenin is controlled by the Wnt signalling pathway and hepatocyte growth factor). The gene for Cdh1 is considered to have tumour suppressor qualities, with mutations in this gene being linked to the progression of a number of cancers. Cdh1 is also known to act as a receptor for the bacteria *Listeria monocytogenes* and the fungus *Candida albicans*. Some viruses interact with proteins involved in junctional complexes, but none is known to interact directly with CDH1 proteins (Yoon and Spear, 2002)

Whilst most animals harbour only one gene for cdh1, the inventors have found that multiple copies of the cdh1 gene are found in the genome of Atlantic salmon, three copies of cdh1 are present. One of these copies is located on Atlantic salmon chromosome 11 (ie ssa11), whereas the two other copies are located within a 50,000 base pair region on Atlantic salmon chromosome 26 (ssa26). The Atlantic salmon genome has not yet been annotated, so that the three different copies of the cdh1 gene do not yet have standard names. Here, the two cdh1 genes on ssa26 will be referred to as cdh1-1 and cdh1-2, while the cdh1 gene on ssa11 will be referred to as cdh1-3. The corresponding protein products will be referred to as Cdh1-1, Cdh1-2, and Cdh1-3. For the purposes of the present invention, when the subject is a salmon, cdh1 may be any one of cdh1-1, cdh1-2, cdh1-3, or any combination thereof. For example, the DNA polymorphism of the present invention may be in cdh1-1. The variant of the present invention may be one or more amino acid position in the protein produce of any of the cdh1 genes mentioned above.

Cdh1, like other members of the cadherin family, are found in many animals. In each animal Cdh1 performs the same role of forming cell-cell adhesions. The utility of the present invention therefore naturally extends to predicting resistance to viral infection in any subject that includes endogenous Cdh1. Consequently, when referring to Cdh1, as part of the present invention, the reference relates to the protein product of the cdh1 ortholog found in the subject that is subjected to the method of the present invention. When referring to cdh1 the reference relates to the cdh1 ortholog found in the subject that is subjected to the method of the present invention. Establishing the ortholog for cdh1 in any given animal is well within the ordinary abilities of the person skilled in the art. For example, irrespective of species, a Cdh1 protein may be defined as a protein, present in epithelial cells, that contains four or five copies of the cadherin tandem repeat domain (which has identifier cd11304, cd00031, or pfam00028 in the GenBank Conserved Domains database, version 3.12), in addition to a Cadherin cytoplasmic region (which has identifier pfam01049 in the GenBank Conserved Domains database, version 3.12), preferably mediating the formation of calcium dependent cell-cell junctions.

Alternatively, a protein-protein BLAST (BLASTP) against the GenBank RefSeq protein database may be used in order to identify a Cdh1 ortholog; if more than 50% of the best hits (i.e. those hits having an E-value of 0.0) are annotated as a cadherin-1 protein or a cadherin-1-like protein, then the query protein is a Cdh1 ortholog), and preferably that mediates the formation of calcium dependent cell-cell junctions.

The GenBank (release 205.0) identifiers of cDNA sequences of some cdh1 orthologs can be found in Table 2. Deduction of the protein sequence corresponding to a cDNA sequence is well within the ordinary abilities of the person skilled in the art. Therefore, only cDNA sequences (not protein sequences) are listed in Table 2.

Alternatively, or additionally the ortholog may be determined to share a 99, 98, 97, 96, 95, 90, 85, 80, 75% sequence homology with any of those sequences identified in Table 2, while mediating the formation of calcium dependent cell-cell junctions. However, without wishing to be restricted further, but in the interest of clarity, the Cdh1 or cdh1 may be any of those identified in Table 2 and that correspond to the subject as indicated in Table 2.

It should be noted that in some species, CDH1 is used as an acronym for another protein which is not an epithelial cadherin, the APC/C activator protein CDH1. Within the present application, Cdh1, and cdh1,CDH1 and CDH1 always refers to epithelial cadherin proteins/genes.

TABLE 2

| cdh1 orthologs | | |
|---|---|---|
| Subject | gene name | GenBank sequence* |
| Atlantic Salmon (*Salmo. salar*) | cdh1-1 | BT058864.1 |
| Rainbow trout (*O. mykiss*) | cdh1 | AB787267.1 |
| Human (*Homo sapiens*) | CDH1 | NM_004360.3 |
| Chicken (*Gallus gallus*) | CDH1 | NM_001039258.2 |
| Pig (*Sus scrofa*) | CDH1 | NM_001163060.1 |
| Cattle (*Bos taurus*) | CDH1 | AY508164.1 |

*All sequences are referred to by their Genbank VERSION identifier. The identifiers given in the table pertain to NCBI-GenBank Flat File Release 205.0 (and, since the VERSION identifier is stable, most likely to any later GenBank release).

For example, the DNA polymorphism can be located on chromosome 26 and within a cdh1 gene of Atlantic Salmon. Such a DNA polymorphism has been shown to capable of predicting resistance to IPN, more particularly by being a causal mutation in the determination of resistance or non-resistance. The Atlantic salmon contains more than one cdh1 gene. In humans, only one cdh1 ortholog is present, and it is located on chromosome 16 (location 16q22.1). In chicken, only one cdh1 ortholog is present, and it is located on chromosome 11.

Each type of DNA polymorphism provided above can be contemplated individually as part of the present invention for the step of determining in the methods of the present invention.

The DNA polymorphisms of the present invention may lie within the coding region of the cdh1. For example, in the case of Atlantic salmon, the DNA polymorphism resides within exon 7 of cdh1-1 (the DNA sequence of cdh1.1 is provided in GenBank (release 205.0) sequence BT058864.1).

The DNA polymorphism may also be any DNA polymorphism that changes the amino acid sequence of the corresponding Cdh1 protein. In particular, the DNA polymorphism may be any DNA polymorphism that causes an amino acid shift in a cadherin tandem repeat domain number 2 within the Cdh1 protein. Alternatively, the DNA polymorphism may be any DNA polymorphism that causes an amino acid shift in one of the other cadherin repeat domain present in the protein in question. Table 1 contains an overview of the positions of the cadherin tandem domains in some relevant cdh1 orthologs.

Consequently, the DNA polymorphism of the present invention may be a DNA polymorphism at position 1065 in GenBank (release 205.0) sequence BT058864.1. When cytosine is present at position 1065 in GeneBank (release 205.0) sequence BT058864.1 the allele is a resistant allele. When thymine is present at position 1065 in GenBank (release 205.0) sequence BT058864.1 the allele is a non-resistant allele. For other animals, the DNA polymorphism may be selected from any of the DNA polymorphism corresponding to position 1065 in GenBank (release 205.0) sequence BT058864.1. Alternatively, the DNA polymorphism may be any DNA polymorphism causing an amino acid shift at an amino acid position orthologous to the amino acid positions being shifted by any of the DNA polymorphism corresponding to position 1065 in GenBank (release 205.0) sequence BT058864.1. FIG. 1A and FIG. 1B displays a multiple alignment of Cdh1 orthologues from several species, illustrating that the positions corresponding to 1065 in GenBank (release 205.0) sequence BT058864.1 can easily and unequivocally be determined in species such as human and chicken. Table 3 displays the positions of nucleotides, within cdh1 orthologs, corresponding to position 1065 in GenBank (release 205.0) sequence BT058864.1, and the positions of other nucleotides causing amino acid changes in the amino acid positions in question.

Establishing the corresponding position for the polymorphisms of the present invention in any given animal is well within the ordinary abilities of the person skilled in the art. However, without wishing to be restricted further, but in the interest of clarity, the polymorphisms may be any of those identified in Table 3 and that correspond to the subject as indicated in Table 3.

TABLE 3

Polymorphisms within cdh1 genes, causing amino acid changes in positions orthologous to the amino acid positions that are affected (changed) by DNA polymorphisms in position 1065 of GenBank (release 205.0) sequence BT058864.1. The positions of the polymorphisms are relative to the beginning of the corresponding mRNA GenBank sequences.

| Subject | GenBank sequence* | Position of poly-morphism(s) | Resistant Allele/non-resistant allele |
|---|---|---|---|
| Atlantic Salmon | BT058864.1 | 1065 | C/T |
| Human | NM_004360.3 | 1085[1], 1086, 1087[1] | |
| Chicken | NM_001039258.2 | 1079[1], 1080 | |
| Pig | NM_001163060.1 | 1066[1], 1067 | |
| Cattle | AY508164.1 | 961[1], 962, 963 | |

*All sequences are referred to by the Genbank VERSION identifier. The identifiers given in the table pertain to NCBI-GenBank Flat File Release 205.0 (and, since the VERSION identifier is stable, most likely to any later GenBank release).

The DNA polymorphisms may also be any DNA polymorphisms that leads to differences in expression levels of a cdh1 gene, or any DNA polymorphisms that causes differential splicing of the transcript of a cdh1 gene.

[1]These positions are direct orthologs of position 1065 in GenBank sequence BT058864.1

Each of the DNA polymorphisms is contemplated individually as part of the present invention.

If an Atlantic salmon has two resistant alleles at the locus corresponding to position 1065 in GenBank sequence BT058864.1, then that animal has resistance to viral infection. If an Atlantic salmon has two non-resistant alleles at the locus corresponding to position 1065 in GenBank sequence BT058864.1 then that animal would not be determined to have resistance to viral infection. If an Atlantic salmon carries one resistance allele and one non-resistance allele, then the animal would be determined to be intermediate in terms of resistance.

For most polymorphic loci (in any species), there will be a number of other loci having identical or highly similar genotype patterns. To illustrate, two loci have identical genotype patterns if all or most animals having genotype AA at locus 1 have genotype CC at locus 2, all or most animals having genotype AB at locus 1 have genotype CD at locus 2, and all or most animals having genotype BB at locus 1 have genotype DD at locus 2. In scientific terms, two such loci will be said to be in strong linkage disequilibrium (LD) with each other. Any DNA polymorphism, being used in testing for (e.g.) resistance to a virus, may be replaced by other DNA polymorphisms with which it is in strong LD. Consequently, the present invention may therefore relate to a method where the two polymorphism (described above) are replaced by other loci with which they are in strong LD. The applicants have identified a number of such loci;—

AGKD01281000.1_4157[T/TA];
AGKD01281000.1_5527[T/TAT];
AGKD01021775.1_19790[G/A].

The above loci are defined with reference to the whole genome sequence for *Salmo salar* published in GenBank under accession number AGKD00000000 (version AGKD00000000.1 GI: 354459050). More particularly, the polymorphisms derive their name as described above from the following: GenBank accession number, followed by underscore ('_') followed by the position of the DNA polymorphism within the GenBank sequence, followed by square brackets enclosing the resistant allele (appearing first) and the non-resistant allele (appearing second). These DNA polymorphisms are in very strong LD with the DNA polymorphism corresponding to position 1065 in GenBank sequence BT058864.1.

For avoidance of doubt, Table 4 contains a list of DNA sequences pertaining to four DNA polymorphisms. The set of four polymorphisms are constituted by 1) the DNA polymorphism corresponding to position 1065 in GenBank (build 205.0) sequence BT058864.1, and 2) the three (above-mentioned) DNA polymorphisms that are in strong LD with the DNA polymorphisms corresponding to position 1065 in GenBank (build 205.0) sequence BT058864.1. Each polymorphism has one allele (sequence variant) corresponding to resistance to IPN and one allele corresponding to susceptibility (non-resistance) to IPN. The sequence numbers are relative to the associated Patent in generated sequence listing.

sequence for Cdh1-1 (ie ACN10577.1, SEQ ID NO. 12). Establishing the corresponding position in the ortholog for any given animal is well within the ordinary abilities of the person skilled in the art. For example, the corresponding position in the ortholog may be determined by using multiple sequence alignment programs such as Clustal Omega. FIGS. 1A and 1B displays a Clustal Omega multiple sequence alignment of the Atlantic salmon Cdh1-1 protein sequence, together with Cdh1 orthologs from human, chicken, pig and cattle, where the amino acids corresponding to position 325 in Cdh1-1 have been highlighted. It is evident from the figure that the positions corresponding to this position, in the different species, can be easily and

TABLE 4

DNA sequences of the DNA polymorphisms corresponding to position 1065 in GenBank (build 205.0) sequence BT058864.1, in addition to the three DNA polymorphisms that are in strong LD with the DNA polymorphisms corresponding to position 1065 in GenBank (build 205.0) sequence BT058864.1. Each polymorphism has one allele (sequence variant) corresponding to resistance to IPN and one allele corresponding to susceptibility (non-resistance) to IPN. The sequence identifiers are relative to associated Patentin generated sequence listing.

| SNP | Resistance sequence variant | Non-resistance sequence variant |
|---|---|---|
| Position 1065 in BT058864.1 | CCAACATGTTTGTCATCAACCCTGTGACTGGAGGGATTCGG, ie SEQ ID No. 1 | CCAACATGTTTGTCATCAACTCTGTGACTGGAGGGATTCGG, ie SEQ ID No. 2 |
| AGKD01281000.1_4157[T/TA] | TATCGAAGTTCTTTTTTTTTTATATGACTATCCTTTGGCA, ie SEQ ID No. 3 | TATCGAAGTTCTTTTTTTTTATATATGACTATCCTTTGGCA, ie SEQ ID No. 4 |
| AGKD01281000.1_5527[T/TAT] | GGACTTTGAGCACGTGTTTTGACGGTGTAGGAAGTTTTTG, ie SEQ ID No. 5 | GGACTTTGAGCACGTGTTTTATGACGGTGTAGGAAGTTTTTG, ie SEQ ID No. 6 |
| AGKD01021775.1_19790[G/A] | GATGACACTAAATCGCAGGGGTGCGCCTGCGTACGTTATGA, ie SEQ ID No. 7 | GATGACACTAAATCGCAGGGATGCGCCTGCGTACGTTATGA, ie SEQ ID No. 8 |

For other animals, the DNA polymorphisms directly affecting resistance to viral infection, ie the causal DNA polymorphisms, are defined above. Other DNA polymorphisms that are in strong LD with these causal DNA polymorphisms are considered part of the present application. Two DNA polymorphisms may be defined as being in strong LD with each other if the square of the correlation coefficient between alleles at the two DNA polymorphisms is larger than 0.7 (this measure is usually denoted $r^2$, and it is a frequently used measure of LD).

The cdh1 polymorphism of the present invention have been found to correspond to variants in the amino acid sequence of Cdh1, which correlate with resistance or non-resistance to viral infection (depending on the amino acid provided in the protein at that position of variance within the amino acid chain). Consequently, analysis of the amino acid sequence for Cdh1 in the subject can assist in predicting resistance.

Optionally, the variant is present in an extracellular portion of CDH1.

For example, in Atlantic salmon the amino acid provided at position 325 in the amino acid sequence for Cdh1-1 has been found to direct resistance or non-resistance to viral infection in the subject. Therefore, determining which amino acid is provided at this position (ie determining the variant at this position) will enable the investigator to determine if the subject is likely to have viral resistance or not.

For other animals, the variant may be found in the corresponding position to position 325 in the amino acid unambiguously determined by visual inspection. Human, chicken, pig and cattle are evolutionary very distant from the Atlantic salmon, yet FIG. 1A and FIG. 1B demonstrates a close inter-species homology. Therefore the corresponding positions should be identified with the same precision in other animal species. The determination of the sequence of a protein is well within the ordinary skills of the art, given that the corresponding cDNA sequence is available. If the corresponding cDNA sequence is not available, it is well within the ordinary skills of the art to obtain that sequence, for example by screening a relevant cDNA library by PCR or hybridisation, using primers or hybridisation probes derived from a cdh1 ortholog from a related species, followed by DNA sequencing of the PCR- or hybridisation-positive clones and validation by nucleotide BLAST against an annotated reference database (such as the NCBI RefSeq database). Alternatively, a relevant cDNA library could be sequenced using next-generation sequencing (RNA-seq), followed by the de novo of the sequence reads into a transcriptome sequence, followed by identification validation of cdh1 genes using nucleotide BLAST against an annotated reference database.

However, without wishing to be restricted further, but in the interest of clarity, the variant may be any of those identified in Table 5 and that correspond to the subject as indicated in Table 5.

Not wishing to be restricted further, but in the interests of clarity, in salmon, when the variant is determined to be proline at position 325 in the amino acid sequence for Cdh1-1, the subject is predicted to have viral resistance. When the variant is determined to be serine at position 325 in the amino acid sequence for Cdh1-1, the subject is predicted not to have viral resistance. Variant identities in other animals are described in Table 5. The amino acid sequence of Cdh1-1 can be found in line 1 ("ssa-1") of the multiple sequence alignment of FIG. 1A and 1B (i.e., SEQ ID NO. 12), position 325 being highlighted in this figure. The corresponding positions within proteins from other species, being orthologues of Cdh1.1, have been similarly highlighted in FIG. 1A and 1B.

TABLE 5

| Subject | GenBank identifier of CDH1 sequence** | Variant Positions | Resistant Variant/ non-resistant variant |
|---|---|---|---|
| Atlantic Salmon (Cdh1-1) SEQ ID NO. 12 | ACN10577.1 | 325 | Pro/Ser |
| Human SEQ ID No. 14 | NP_004351.1 | 321 | Arg* |
| Chicken SEQ ID No. 13 | P08641.2 | 327 | Arg* |
| Pig SEQ ID No. 15 | NP_001156532.1 | 321 | Ser* |
| Cattle SEQ ID No. 16 | NP_001002763.1 | 321 | Lys* |

*Only one amino acid variant is known.
**All sequences are referred to by their Genbank VERSION identifiers. The identifiers given in the table pertain to NCBI-GenBank Flat File Release 205.0 (and, since the VERSION identifier is stable, most likely to any later GenBank release).

In any species, the DNA polymorphism, or DNA polymorphisms, causing viral resistance, may be any DNA polymorphism(s) that causes an amino acid shift in a Cdh1 ortholog. Alternatively, the DNA polymorphism may be any DNA polymorphism(s) that causes variation in the expression levels of a cdh1 gene, i.e. any DNA polymorphism that takes part in regulating expression levels of a cdh1 gene. This includes both DNA polymorphisms within cis-acting loci regulating a cdh1 gene (DNA polymorphisms located on the same chromosome as the cdh1 gene, targeted by transcription factors and other regulatory proteins) and DNA polymorphisms located within genes encoding transcription factors or other regulatory factors binding to the regulatory regions of the cdh1 gene (trans-acting DNA polymorphisms). The DNA polymorphism(s) may also be any DNA polymorphism(s) that cause alternative splicing of cdh1 exons or any other differences in the protein sequence of, or abundance of, a Cdh1 protein.

In particular, the DNA polymorphism(s) may, in any species, be DNA polymorphisms causing amino acid shifts within the second cadherin repeat of a Cdh1 protein. The cadherin repeats are extracelluar, $Ca^{2+}$-binding domains within the Cdh1 proteins, known to be involved in protein dimerisation. Position 325 within Cdh1-1 is located within the second cadherin domain of Cdh1-1.

The step of determining the presence or absence of the polymorphism or variant in a subject may be practised on a sample taken from the subject. The sample may be any sample in which analysis of nucleic acid or protein material is possible, as would be readily understood by the person skilled in the art. For the avoidance of doubt, the sample may be a muscle tissue sample, blood sample, liver sample and/or a fin clip.

As mentioned above, cadherin is known to have a central role in the formation of tight cell-cell adhesions. Consequently, after realising the link with viral resistance, it is reasonable to derive from the collected understanding of the physiological role of cadherin that viral resistance may be achieved by a variant form of cadherin that is able to maintain a tighter cell-cell adhesion than other forms of the protein, and thereby restrict the ability for virions to enter into inter-cellular spaces in order to locate their docking proteins. Consequently, the present invention would be expected to have broad applicability to any virus. Not wishing to be restricted further, but in the interest of clarity, the viral infection may be bursal disease (IBDV), infectious pancreatic necrosis (IPN), pancreas disease (PD), heart and skeletal muscle inflammation (HSMI), infectious salmon anaemia (ISA) and cardiomyopathy syndrome (CMS).

The skilled person would be well aware of all available methods capable of testing for the presence or absence of a DNA polymorphism. For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), or competitive hybridisation of probes complementary to the different alleles (e.g. the TaqMan assay from Applied Biosystems).

Consequently, in a further aspect of the present invention, there is provided a hybridisation probe that is specific for one or more of the aforementioned DNA polymorphisms.

Hybridisation probes that are selective for these DNA sequences may form part of the present invention.

PCR-primers and extension primers used in order to genotype the DNA polymorphisms of the present invention (ie determining which alleles of the polymorphisms are present in any given individual) may form part of the present invention. For example, primers suitable for genotyping the polymorphism corresponding to position 1065 within GenBank (release 205.0) sequence BT058864.1 are listed in associated sequence listing More specifically, the forward PCR primer, the reverse PCR primer, and the extension primer used in order to genotype the polymorphism corresponding to position 1065 within GenBank (release 205.0) sequence BT058864.1, on the iPLEX System from Sequenom (San Diego, Calif., USA) are listed as SEQ ID No. 9, 10, and 11 within the associated sequence listing, respectively.

```
                                          SEQ ID No. 9
acgttggatg ctcactctgt ttaggtgacg SEQ ID No. 10
acgttggatg attaacccga atccctccag SEQ ID No. 11
gatccctcca gtcacag
```

A subject that is predicted to have resistance to infectious pancreatic necrosis according to the first aspect of the present invention is more likely than normal to produce offspring that have a higher than normal chance of having resistance to viral infection. Consequently, in a further aspect of the present inventions, there is provided a method of selecting a non-human subject for use as broodstock, wherein the non-human subject is selected, based on the prediction by the method as claimed in the first aspect of the present invention, to have resistance to viral infection.

Conversely, a non-human subject predicted by the method of the first aspect of the present invention as not having resistance to viral infection would not be selected as broodstock.

The present invention also relates to an isolated polynucleotide comprising one or more of the single DNA polymorphisms provided above.

The realisation that specific forms of the protein cadherin is implicated in conferring viral resistance to a subject, provides an understanding of the therapeutic utility for cadherin in gene therapy. Further work carried out by the inventors support this conclusion. The inventors have been the first to demonstrate that the viral resistant form of cadherin prevents cell invasion by virions. Furthermore, the inventors have been the first to demonstrate binding of virion to cadherin. Consequently, in a further aspect of the present invention, there is provided a composition comprising an agent capable of inducing the expression of the resistant form of Cdh1 in a cell to which the composition is administered, and/or an agent capable of preventing the expression of the non-resistant form of Cdh1 in a cell to which the composition is administered. For example, an agent capable of inducing the expression of the resistant form of Cdh1 in a cell to which the composition is administered may comprise a nucleic acid molecule encoding Cdh1 that includes the resistant variant at 1 or more amino acid position of cadherin, and or an agent capable of editing the gene for Cdh1 from the non-resistant to resistant form (eg using CRISPR procedures). For example, an agent capable of editing the gene for Cdh1 from the resistant to resistant form (eg using CRISPR procedures). Also contemplated as an aspect of the present invention is a pharmaceutical composition comprising any of the aforementioned compositions and any or all of a pharmaceutically acceptable carrier, excipient, and/or diluent. Also contemplated as an aspect of the present invention is a composition comprising either or both of the aforementioned agents for use in a method of treatment. The method may be a method for treating viral infection. The method of treating may be prophylactic or otherwise.

In a further aspect of the present invention, there is provided a method of treating viral infection by administering to a subject an effective amount of a composition comprising a nucleic acid molecule encoding cadherin that includes the resistant variant at 1 or more amino acid position of cadherin.

All features of the first aspect of the present invention may apply equally to the second or further aspects of the present invention. For example, the cadherin referred to in the aspects of the present invention after the first aspect may be any cadherin mentioned above, for example Cdh1.

The form of composition used in the above pharmaceutical composition and in the above described methods of treatment that are dependent on the method employed to transfer the gene into the host cell in the subject to be treated would be familiar to the skilled person. There are essentially two methods, one that involves the combatant viral vectors to transfer the gene into the host cell (ie the composition would comprise a recombinant viral vector that includes the aforementioned nucleic acid sequence), the second involving naked DNA or DNA complexes.

Methods for preparation and administration of nucleic acid molecules are explained in detail in experimental manuals (Supplement of Experimental Medicine, Basic Technology in gene therapy, Yodosha (1996); Supplement of Experimental Medicine, Experimental Methods in Gene Introduction and Expression Analysis, Yodosha (1997); Handbook for Development and Research of Gene Therapy, Japan Society of Gene Therapy ed., NTS (1999)).

Illustrative methods of non-vector gene transfer into cells include the lipofection method, calcium phosphate co-precipitation method, DEAE-dextran method, direct DNA introduction methods (potentially using micro glass tubes) and the like.

Representative methods that use viral vectors include those using viral vectors such as recombinant adenovirus, retrovirus and the like. More specifically, the gene of interest can be introduced into a DNA or RNA virus such as detoxified retrovirus, adenovirus, adeno-associated virus, herpes virus, vaccinia virus, poxvirus, poliovirus, Sindbis virus, Sendai virus, SV40, human immunodeficiency virus (HIV) and the like, which is then infected to the cell to introduce the gene into the cell.

As methods of introducing a gene therapy agent into a patient, there are in vivo methods, which permit direct introduction of the gene therapy agent into the body, and ex vivo methods, in which certain cells are removed from human, to which the gene therapy agent is introduced and which are returned into the body thereafter (Nikkei Science, April 1994 issue pp. 20 24; Monthly Yakuji, 36(1): 23 48 (1994); Supplement To Experimental Medicine 12 (1.5) (1.994); Handbook for Development and Research of Gene Therapy, NTS (1999)). According to the present invention, the in vivo method is preferred.

Dosage forms may take various forms according to various administration regimens described above (for example, liquids). When, for example, an injection containing the gene as an effective ingredient is to be used, said injection may be prepared by dissolving the effective ingredient(s) into a standard solvent (a buffer such as PBS, physiological saline, sterile water, etc.). The injection liquid may then be filter-sterilized with filter as needed and then filled into sterilized containers, Conventional carriers and so on may be added to the injection. Liposomes, such as HVJ-liposome, may take the form of suspensions, frozen formulations, centrifugation-concentrated frozen formulations, and the like.

Proper methods and sites for administration adequate for the disease or symptom to be treated are selected for the gene therapy agent of this invention. As to the administration methods, parenteral administration methods are preferred.

Examples of parenteral administration methods include administration by noninvasive catheter, noninvasive injector and so on. More preferred are administration methods which utilize noninvasive catheter, noninvasive injector and such under the usage of echo.

The term "DNA polymorphism allele" takes its normal meaning as would be well understood by the person skilled in the art. However, for the avoidance of doubt "DNA polymorphism allele" may mean one of two different nucleotide sequences at the site of a DNA polymorphism of the present invention (one allele being the "resistance allele", the other being the "non-resistance allele")

The NCBI-GenBank Flat File Release 205.0 sequence BT058864.1 is the following:

```
                                          SEQ. ID. NO. 12
  1 acacgtttga aaaatagact tttctcatct acacgtaaag
    ggattacttg ttactattgg 61 tggaacgact atccaaaaat tattcaaaac aaatgggggc
    attttggttc gtggagttgg 121 gcgtattaat attatttctc caggctttca aaccagggtc
    gtcggagtca acatgtctac 181 caggtttcaa ttcagaaata tacattttca aagtggaaag
    aaatcactta caaagtggcc
```

-continued

```
 241 ggagactagg aaaagtggtt tttgatgact gcaccagccg
     caccagcttt ctctttcact 301 ccgaggattc acacttcaaa gtagatggcg acgggacgct
     gaaactggag aggggggctga 361 ctctgcataa tggacataag gaggtctatg tctctaccca
     gtccaagggc aagaagatca 421 cggttccagt cagagtgctg catgaggcca gacatggcca
     ccaccacaat caccatgaga 481 tgaccaccca gcccaagcca ggagcaagtc tgtctctacc
     tgttctgaac ttccccaagt 541 cttcaggagg tctgaaaaga aggaagaggg actgggtcat
     tcctcccatc aacttccag 601 agaatgaccg aggcccttc cccaagatta tggtgcagat
     caggtccaac aatgataaag 661 aggtgaagat ccagtacagc atcactggca ctggggcaga
     cctacctcct gtgggaatct 721 tcactgtgga caaaaactct gggaatctct atgtgaccga
     gcccttggac agggagaaaa 781 aagacaaata cattctccta gcccatgctg ttgcagtggg
     tgcaggtata gctgaggatc 841 ccatggagat cattgtgaaa gtcatcgata tgaatgacaa
     caaacctgta tttacccaag 901 atccatttat gggaacagtt cctgaagcat caaaaccagg
     tgacgaggtc atgcaggtaa 961 cggccactga tgctgatgag gagggctctg ccaattctga
     tgtcagatac accattctca 1021 gtcaggagcc tccactacca agccccaaca tgtttgtcat
     caactctgtg actggaggga 1081 ttcggggttaa tgcacctggg ttggacagag agaaaattcc
     caaatatact ttggcaatcc 1141 aagctgccga tatggaggga aatggcctta ccagctttgg
     caaagccatc attacactaa 1201 cggacagcaa tgacaacgcg ccacagtttg tgacgccttc
     gtacaccgtg tcagtccag 1261 agaataaagt ggatgccttg gtggtgaaaa tgccagtgac
     tgatggagat gagcctcact 1321 cctctgcctg ggccaccacc tacaagatag ttgacgggga
     ccctcaaggc cttttcaacg 1381 tgagcacagg ccctagcaag ctggagggca tcattacaac
     agccaagccg cttgactttg 1441 agaagaacaa caagtacact ctgctggtca ctgtgcagaa
     tgaagtccca ttcacaatca 1501 gcatgcccac ctccactgct actgttgtag tgaatgtgga
     ggatgtgaat gaagctccag 1561 tcttcacccc agtggagaag attatcagga aacctgagga
     cctccctgtt gacagtgacc 1621 tggttctgta cacagccaca gacccagaca ccgcaaggaa
     tcagaaagtc acatacaaga 1681 tacgcaatga taatgctgga tggctcagta tcaacaaaga
     cactgggctg atcaaagtca 1741 agagcctcat ggacagaaa tccacttttg tccaagacaa
     caaatactct gttattgttc 1801 tgggcatcga caacgatgaa atcccggcaa ctggcactgg
     caccccttatc atagagctgg
```

```
1861 aggatgtgaa tgataatgct ccaaccattg acgagagtgt
     gatcagggtc tgcaacaagg 1921 agtcctcccc acagttgttg tcagtcactg ataaagatgg
     tgcgggcttc actgctccat 1981 acaccgtaca gcttcagggg tcgtcccatt ctaactggac
     tgccagaatg aacgacacaa 2041 agactggcat tatcctgact ctgaagacta tgttggacag
     tggagattac acggttgtcc 2101 tgagagtgtc tgacaaccag ggcctgcacc atgacagcac
     catccaggcc tccgtctgtg 2161 actgcaaagg agcggatgtc cagtgctccg ataaagctgt
     agcaggcttc ggcatctcta 2221 gcattctggg aattctagga gcagtcttac tactcctatt
     gttgtctctt ctgctgctca 2281 tgttcctgag gaagagaggt ggcgagaaga aggagcctct
     gctgcaggag gacgatgtca 2341 gggacaacat ctactactat gacgaggagg aggtggcga
     ggatgaccag gatttcgact 2401 tgagcgttct gcacagaggt ctggataacc gtcctgatgt
     tttccgtaat gacatcgctc 2461 caaccatggc ccggccagag tatcgtccac gacccgccaa
     cccagccgac attggcaact 2521 tcattgatga taacctgaag gcagctgaca cgacccccac
     tgctcctccc tacgactccc 2581 tcctggtgtt tgactatgaa ggaggtggct ctgaggctgg
     ctcccctcagt tccctcaact 2641 cctccagctc aggagacgac caggactacg acctccttca
     agagtgggc ccgcgcttca 2701 agaagctgtc tgacatgtac ggaggaggag aggattgaga
     agtcagtcag ccactaaacc 2761 tttttgcttg gaaactgtcc ggttctccac actttggtct
     gtaaactgaa gaccttttct 2821 ttatttcccc tttttatgcg tttcgggcac atttacagtt
     tggcaatttg atttgtgcag 2881 acatgggacc attttagaaa aaatgtgttc aatgctcgtc
     ttcagcatgg ggagggtggc 2941 atactcttgg ctctgcacta gcaggatgtt gacatggatt
     ttacacaatt cagcagttct 3001 ttctaatgga ctcttaacaa ccccagattg tacttgaatt
     taatatgctt cttttggcgt 3061 cgtatcgaag ttcttttttt ttatatatga ctatcctttg
     gcatgaaatt gaagttactg 3121 aaagccaaat cagccttacg atgttttttgt taactgagat
     taattatcaa gctcaataaa 3181 tgcttttaaa aatgtttgat aaacaactaa gtttgggttg
     ttttattcct tttcattta 3241 atcatattaa tcactaatta tatattttt tcctgaagaa
     gctcacagtt ctgcttttta 3301 ttttattaca gttctgcttt tttaaattaa agatatcctt
     ttggtacaat gatggatgtg 3361 aatatttgta ttaaatacat tgtaatttgt cttatttttga
     gctcaattat tcaaattcac
```

-continued

```
3421 agctgagaca ctagatggcg acaattgaat aaaacaggtc
     ttggtcaatg aaaaaaaaaa 3481 aaaaaaaaaa aaaaaaaag a, i.e.,.
```

The term "ortholog" takes its normal meaning as would be well understood by the person skilled in the art. However, for the avoidance of doubt, the term may mean a any gene found in one species that corresponds to a gene found in another species and wherein both genes share the same function (eg ability to form cell-cell adhesions) and share a common ancestor.

BRIEF DESCRIPTION OF THE DRAWINGS

The present invention will now be described by way of example with reference to the accompanying figures, in which: —

Figure 1A:
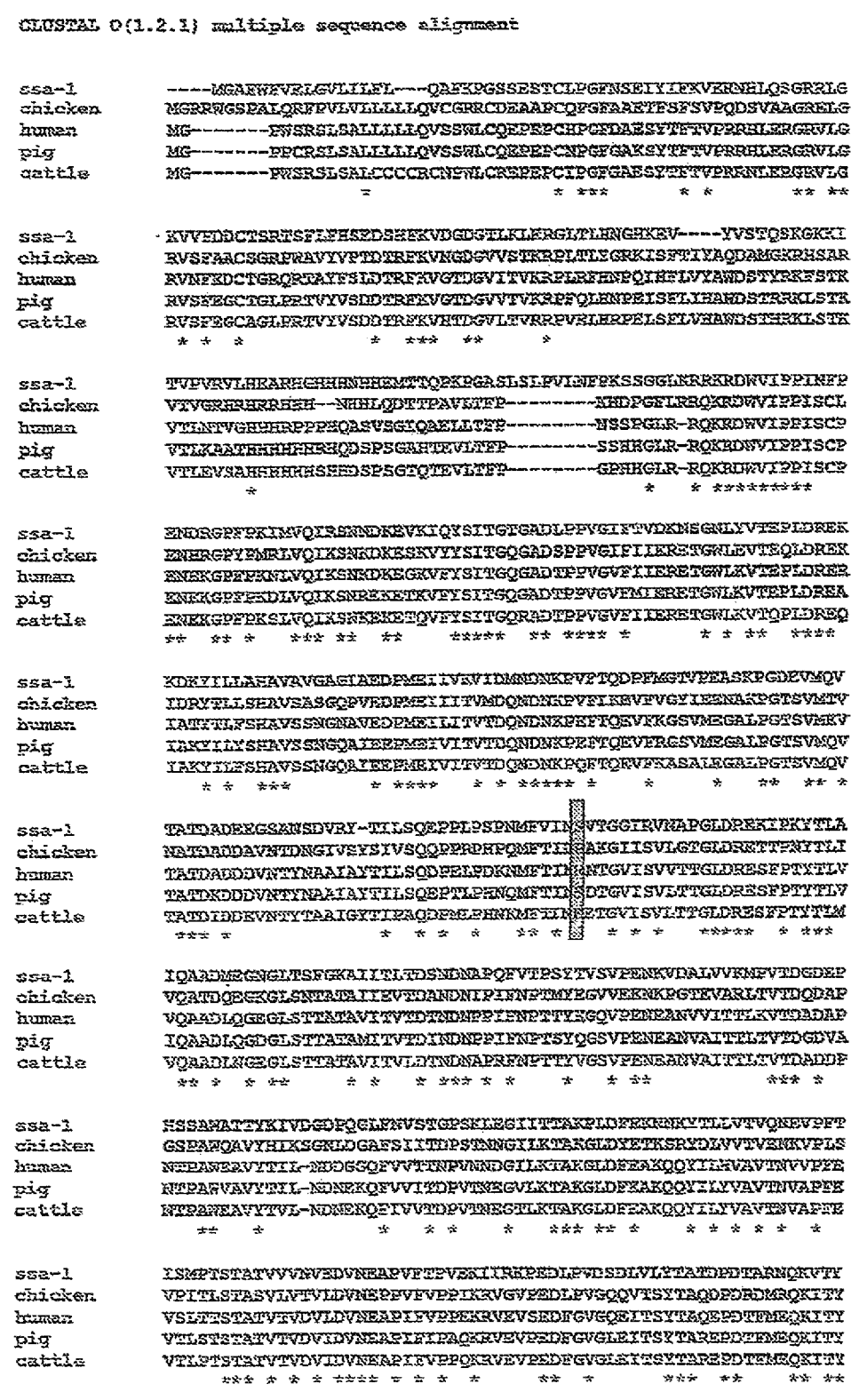
Figure 1B:
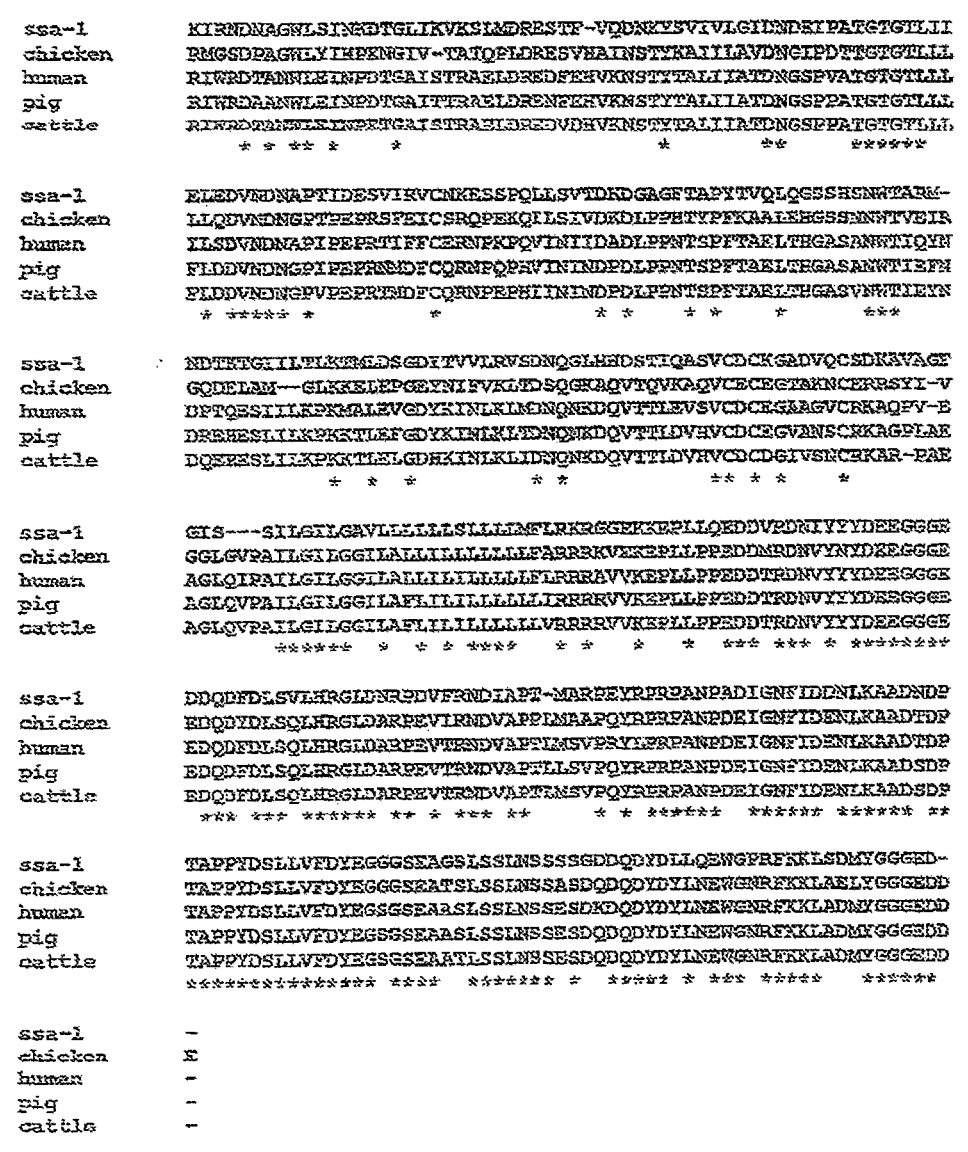

FIG. 1A and 1B provides a multiple alignment of cadherin proteins from different species. 'Ssa-1' is the protein sequence of Cdh1-1 from Atlantic salmon (i.e., SEQ ID No. 12), while 'Chicken' (i.e., SEQ ID No. 13), 'Human'(i.e., SEQ ID No. 14), 'Pig'(i.e., SEQ ID No. 15), and 'Cattle' (i.e., SEQ ID No. 16) are, respectively, the protein sequences of Cdh1 (epihelial cadherin) orthologs from *Gallus gallus, Homo sapiens, Sus scrofa* and *Bos Taurus*. The GenBank (release 205.0) identifiers of the salmon ('Ssa-1', Chicken, Human, Pig, and Cattle sequences of FIG. 1A and 1B are, respectively, ACN10577.1 (i.e., SEQ ID No. 12), P08641.2 (i.e., SEQ. ID No. 13), NP_004351.1 (i.e., SEQ ID No. 14), NP_001156532.1 (i.e., SEQ ID No. 15), and NP_001002763.1 (i.e., SEQ ID No. 16).

1. CONSTRUCTING A REFERENCE SEQUENCE OF THE QTL REGION

Figure 2:
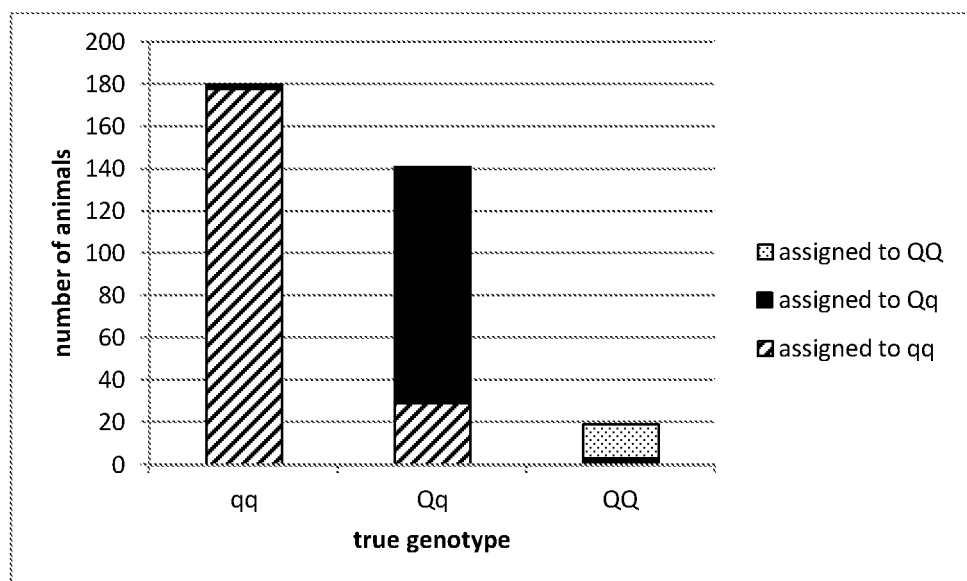
FIG. 2 provides a graph showing the relationship between true genotype and assigned-to genotype (the genotype the animal was assigned to using the DNA polymorphism corresponding to position 1065 of BT058864.1 (BT058864.1_1065-TC)), for 340 animals from the Aqua-Gen breeding nucleus.

A QTL for resistance to IPN was earlier detected on Atlantic salmon chromosome 26 (Houston et al. 2008, Moen et al. 2009). At the onset of the study described in the present application, we assumed that the QTL was caused by a single, underlying (causative) mutation. Furthermore, we assumed that this causative mutation had two alleles, one allele (Q) that is associated with resistance to IPN and one allele (q) that is associated with susceptibility (non-resistance). Thus, individual animals could be assigned (through the analysis of extensive genetic data sets) a QTL genotype reflecting which combination of QTL alleles (QQ, Qq, or qq) the animals harboured.

The QTL region was defined as the region of the Atlantic salmon genome wherein it was expected, based on earlier results (Moen et al., 2009), that the causative mutation(s) underlying the QTL would be located with a close to 100% probability. More specifically, the QTL region was defined as the region in between the SNPs ESTNV_31602_808 and GCR_cBin30387_Ctg1_91 on the Atlantic salmon SNP linkage map (Lien et al., 2011). The Atlantic salmon genome had at the time not yet been sequenced. In order to identify the causative mutation(s), we therefore needed to construct a reference sequence of the QTL region. Bacterial Artificial Chromosome (BAC) clones matching the two above-mentioned SNPs were isolated from an existing BAC library (Thorsen et al., 2005). On the basis of a physical map made from this library (www.asalbase.org), a minimum tiling path of 31 BACs was made, connecting the two flanking BACs[1]. Atlantic salmon genomic DNA was extracted from each BAC. An individually tagged paired-end library (with average insert size 350 bp) was made for each BAC DNA sample, whereupon the samples were sequenced on a HiSeq 2000 machine (Illumina Inc., San Diego, USA) to an average depth of approximately 800 times haploid genome coverage. Following removal of residual adapter sequences, discarding of too-short reads, trimming of the ends of poor quality reads, and matching of paired-end reads, a de novo assembly was made within each BAC using the 'clc_novo_assemble' program from the CLC Assemble Cell suite (CLC Bio, Aarhus, Denmark). Phrap version 1.090518 (phrap.org) was then used to assemble individual BAC contig sequences into a set of contigs spanning all BACs. Finally, the contigs from this reference were combined into one contiguous genomic sequence by aligning it with scaffolds from a preliminary version of the Atlantic salmon genome sequence (which had been made in-house, using the Celera Assembler software, based on the data from the first 27 batches of sequences submitted by the sequencing project into the NCBI Trace Archive). This genomic sequence will hereafter be referred to as the 'Reference Sequence'.

[1] The minimum tiling path consisted of the following BACs: S0042J22, S0004K18, S0161O04, S0243D12, S0076E15, S0021H01, S0162F10, S0258L08, S0119L01, S0026N22, S0162J03, S0259M06, S0120O19, S0048P16, S0170B06, S0262M03, S0126K07, S0063G22, S0201A04, S0282P22, S0457C13, S0066E05, S0215J07, S0344A15, S0001F22, S0115B04, S0227H08, S0449E20, S0001N03, S0160J02, S0236E20. Information regarding the BACs can be found on www.asalbase.org.

2. SELECTION OF ANIMALS FOR NEXT-GENERATION SEQUENCING

Forty-five Atlantic salmon from the Norwegian breeding nucleus of Aqua Gen AS were chosen for massive parallel sequencing on Illumina HiSeq 2000. These 45 salmon were all selected from among the parents of the 2005 and 2008 year classes of the Aqua Gen breeding nucleus. All salmon in the Aqua Gen breeding nucleus are descendants of salmon taken from Norwegian rivers. The selection of animals was done as described in the following paragraph.

Four hundred and fifty-four full-sib groups of Atlantic salmon fry were IPN-challenged in individual tanks shortly after start feeding (the protocol for the challenge test can be found in Moen et al., 2009). The parents of these full-sib groups (hereafter referred to as 'the mapping parents') would become very central to the study described in this application. Full-sib groups consisted of 103 fish (on average), and tissue samples were collected from the 10 first-to-die within the group as well as 10 survivors (or 10 last-to-die), whereupon DNA was extracted using the DNAeasy kit from QIAGEN (QIAGEN, Venlo, the Netherlands). From 206 selected full-sib groups, affected and surviving offspring were genotyped with three microsatellite markers located within the QTL region, Alu333, Ssa0384BSFU/ii and Ssa0285BSFU, whereupon the linkage phase between alleles of the three microsatellites were identified in each mapping parent using the observed co-segregation of alleles from parents to offspring (genotyping of microsatellite markers are discussed in more detail in abovementioned Moen 2009 article). This genotyping was done in an iterative fashion so that, ultimately, almost all full-sib groups that were likely to have at least one QTL-heterozygous parent (see below) were genotyped. A chi-square test was applied in order to test for co-inheritance of the three-microsatellite haplotype and the affected/resistant phenotype, leading to the identification of 110 QTL-heterozygous mapping parents. Using data from these QTL-heterozygous mapping parents, a table was created linking alleles at the three-microsatellite haplotype to QTL alleles. (If a three-microsatellite allele was found to be linked to both Q and q, only the most prevalent linkage phase was entered into the table). This table was next used to extrapolate QTL genotypes in the mapping parents found to be QTL homozygous, as well as for other animals from the Aqua Gen breeding nucleus. Twenty-two Aqua Gen animals deduced in this way to have the QTL genotype QQ (i.e. expected to provide good IPN resistance), as well as 23 Aqua Gen animals likewise found to have the qq genotype (i.e. expected to provide poor IPN resistance), were chosen for subsequent whole-genome sequencing. These sets of 22 and 23 animals were put together in such a way as to minimise the relatedness of animals within group, by maximising the diversity of three-microsatellite alleles within each group.

3. NARROWING DOWN QTL REGION BY NEXT-GENERATION SEQUENCING

The above-mentioned 23 QQ animals and 22 qq-animals were sequenced using HiSeq2000 technology from Illumina. Individually tagged paired-end libraries were made from each sample, before samples were pooled for sequencing. A total of $264 \times 10^9$ reads was produced, corresponding to a per-animal coverage of two times the haploid genome. The reads were aligned to the reference sequence using bowtie2 with default settings (both unpaired- and paired-end alignments were performed), thereafter removing alignments having Phred-scaled p-value below 30, using the 'view' function of samtools. The reads were aligned pool-wise, i.e. all reads from QQ animals were part of one assembly, and all reads from qq animals were part of another assembly. SNPs and short insertion/deletions (indels) were identified with freebayes (arxiv.org/abs/1207.3907)) using the following string to set the value of parameters relevant to the alignment: "--use-best-n-alleles 2--read-max-mismatch-fraction 0.02--min-alternate-total 3--no-marginals--left-align-indels--pooled--ploidy 90" (see wiki.gacrc.uga.edu/wiki/Freebayes for explanations of the parameters). A Fisher's exact test was used in order to test for independence between QTL allele and SNP/indel allele within reads. The SNPs with the most significant statistics from this test were genotyped in the 110 QTL-heterozygous mapping parents mentioned above, as well as in the challenge-tested offspring of those animals, and a Fisher's exact test was performed on parental haplotypes derived from this data set in order to test for independence between SNP alleles and QTL alleles. The correlation coefficient ($r^2$) between alleles at the SNP and at the QTL, a measure of the degree of linkage disequilibirum (LD) between loci, was also calculated for each SNP, using the 'LD' function of the 'genetics' module of the R statistical program suite. These analyses identified one SNP and two indels whose genotypes were most strongly (among all the tested polymorphisms) associated with deduced genotypes at the QTL. These polymorphisms were in perfect linkage disequilibrium (LD) with each other, and their co-segregation with the QTL was highly significant (P-value=$1.62 \times 10^{-28}$, Fisher's exact test for association between QTL-allele and SNP/indel-allele in haplotype copies derived from QTL-heterozygous mapping parents). The correlation coefficient ($r^2$) between alleles at the QTL and alleles at the SNP/indel was 0.57. The SNP and the two indels resided within a 26 kbp region that contained two full-length genes, one epithelial cadherin gene (cdh1-1) and the gene fam96b. In addition, a truncated (lacking several exons) epithelial cadherin gene (cdh1-2) was noted upstream of cdh1-1.

4. IDENTIFICATION Of BT058864.1_1065-TC

Cdh1-1 is a salmon version, located on chromosome 26, of a protein known to be responsible for $Ca^{2+}$-dependent cell-cell adhesion in epithelial tissue in a variety of species. As noted above, we identified one SNPs and two indels in close proximity to this gene. These three polymorphisms were the subject of our earlier patent application.

Cdh1-1 was amplified and sequenced, using cDNA from 29 different QQ or qq Atlantic salmon from the Aqua Gen population as template. The QTL genotype of the animals had been deduced using a three-microsatellite haplotype as described above. The cDNA was derived from mRNA extracted from samples taken from adult salmon or from salmon fry sampled during a challenge test for IPN-resistance. Eleven different fragments were PCR-amplified, using 11 different primer pairs. The PCR primers were constructed so that there were, for every primer, at least two nucleotide mismatches between the primer sequence and the nucleotide sequence of a third copy of the epithelial cadherin gene, located on chromsome 11 (referred to above as the cdh1-3). The PCR products were direct sequenced using the BigDye Terminator v3.1 Sequencing Kit (Applied Biosystems, Carlsbad, USA) on an Applied Biosystems 3730 DNA Analyzer. The phredPhrap.pl script, employing Phred and Phrap (phrap.org/phredphrapconsed.html), was used for base calling, quality value assignment, and alignment of reads. PolyPhred (droog.gs.washington.edu/polyphred/) was used for variant detection, and consed (phrap.org/phred-phrapconsed.html) was used for visualization of contigs and PolyPhred-detected variation.

Based on the DNA sequences of the amplified fragments, a SNP emerged as displaying a particularly large contrast between the two genotype groups. The position of the SNP corresponded to position 1065 within GenBank sequence BT058864.1, and it had two alleles, thymine and cytosine. Hence, the SNP will be referred to as BT058864.1_1065-TC from now on. BT058864.1_1065-TC had genotype TT in all 17 qq animals, and genotype CC in all but two of the 12 QQ animals (the deviant QQ animals had genotypes TT and CT). BT058864.1_1065-TC was thereafter genotyped in 340 parents of the 2005 year class of the Aqua Gen breeding population, including most of the QTL-heterozygous mapping parents mentioned above; these 340 animals had all been given a 'true' QTL genotype as described above. Assuming that BT058864.1_1065-TC genotypes TT, CT, and CC corresponded to QTL genotypes qq, Qq, and QQ, respectively, 306 out of 340 animals were assigned to the correct genotype (FIG. 2). These results showed that genotypes at BT058864.1_1065-TC are strongly correlated togenotypes at the QTL.

Based on the same data, BT058864.1_1065-TC was also found to be in perfect linkage disequilibrium with the three above-mentioned DNA-polymorphisms already found to be strongly correlated to IPN. Unlike these 3 DNA polymorphisms, however, BT058864.1_1065-TC leads to a change in the amino acid sequence of Cdh1-1. The SNP gives rise to a proline-to-serine shift on a surface-exposed part of the second extracellular cadherin (EC) domain of the protein (also called cadherin tandem repeat domain). Proline is an amino acid that puts conformational restrictions on the proteins it is a part of, due to the unusual structure of the amino acids side chain. It is therefore likely that the proline-to-serine amino acid shift will have major consequences for the properties of the protein.

5. DEMONSTRATING REDUCED MORTALITY RATE AND REDUCED VIRUS COUNTS IN SALMON CARRYING THE IPN RESISTANCE ALLELE

A challenge test was performed on Atlantic salmon fry descending from the Aqua Gen breeding population. Fry at an average weight of 0.2 grams at start feeding were transferred to the research station (Havbruksstasjonen, Tromsø, Norway) and allowed one week of acclimation before challenge. The trial was conducted by Nofima AS (Tromsø, Norway).

Figure 3:
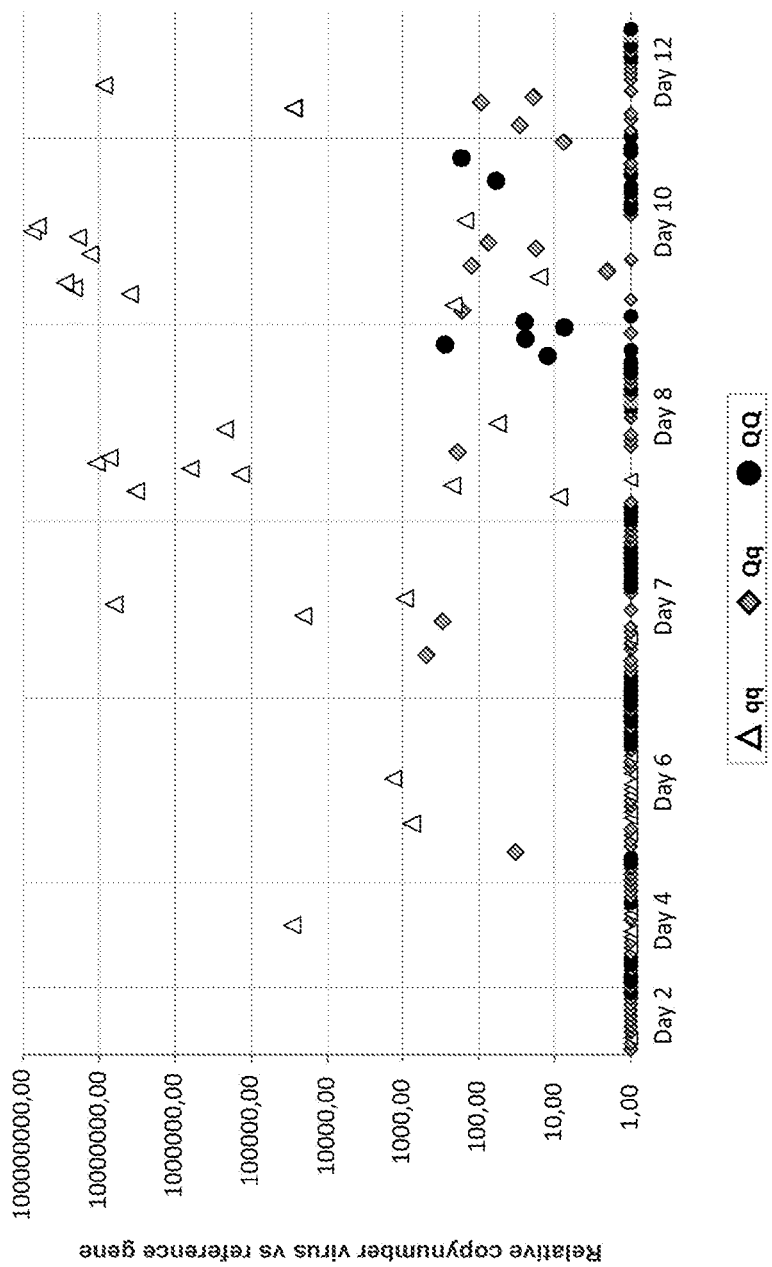
FIG. 3 shows the IPN virus levels (Ct-values after Taq-Man® real-time assay for IPNV) in fish of different genotypes (at the DNA polymorphism corresponding to position 1065 of BT058864.1 (BT058864.1_1065-TC)) sampled at day 2, 4, 6, 7, 8, 10 and 12 after experimental challenge. Given the threshold of the diagnostic test, samples are negative after 37 cycles, and for display purposes negative fish are given a value of 1. Values are normalized against the expression of the reference gene elongation factor 1-alpha. qq=no copies of the resistance allele at BT058864.1_1065-TC, Qq=one copy of the resistance allele at BT058864.1_1065-TC, QQ=two copies of the resistance allele at BT058864.1_1065-TC.

Sixteen hundred fry belonging to three different groups of fish were included in the study, which was performed in eight different tanks, 200 fry in each tank. The three groups differed in the frequency of the IPN resistance marker (ie BT058864.1_1065-TC); Resistant group, frequency of beneficial allele 0.84, Intermediate group, frequency of beneficial allele 0.45, and Susceptible group, frequency of beneficial allele 0.22. The fry were bath challenged by adding infectious pancreatic necrosis virus at a concentration of $10^5$ $TCID_{50}$/ml water. Normal flow was paused while the water was aerated, resuming flow after three hours. Fish were sampled at day 2, 4, 6, 7, 8, 10 and 12 post challenge. The livers of the sampled fish were carefully dissected and placed in RNAlater (Qiagen) for later determination of viral load (see below). The trial was terminated 34 days after challenge. At termination, 10 surviving fry from each of the eight tanks were sampled for determination of carrier status. The tails of all sampled fish were frozen before DNA extraction and subsequent deduction of QTN-alleles. In the Resistant group, the mortality associated with IPN was only 1.3%. In contrast, the IPN-related mortalities in the Intermediate and Sensitive groups were 22.3% and 52.5%, respectively demonstrating how marker-assisted selection significantly reduce the number of IPN-induced mortalities. In order to assess whether the fish were able to resist infection or merely to survive an infection, IPN virus was quantified in survivors from the challenge test, using a Taq-Man real-time RT-qPCR assay provided by an accredited commercial lab (PatoGen Analyse AS, Ålesund, Norway) and compared to the expression of a reference gene (elongation factor 2-α). Among survivors from the Sensitive, Intermediate, and Resistant groups, 90%, 60%, and 10% were carriers of the virus. A similar trend was found in samples taken from days 2, 4, 6, 7, 8, 10 and 12 post infection (dpi), with only qq fish displaying the high virus levels characteristic of diseased/moribund fish (see FIG. 3). QQ fish exclusively found in the Resistant group were predominantly negative, except for a few positive fish with very low virus levels, whereas heterozygous fish (representing both alleles) had intermediate levels. The results thus indicated that the Q alleles act by preventing the virus from infecting cells, rather than helping the fish to survive in the presence of infection.

6. TESTING IPNV INFECTION

The inventors have shown that Atlantic salmon that have been predicted, as described above, to be resistant to IPN, are much more resistant to IPN than Atlantic salmon that have been predicted not to be resistant to IPN. Furthermore, they have shown that the IPN virus does not enter hepatocytes cultured in vitro from resistant salmon, whereas it does enter hepatocytes similarly cultured from susceptible cells.

Figure 4:
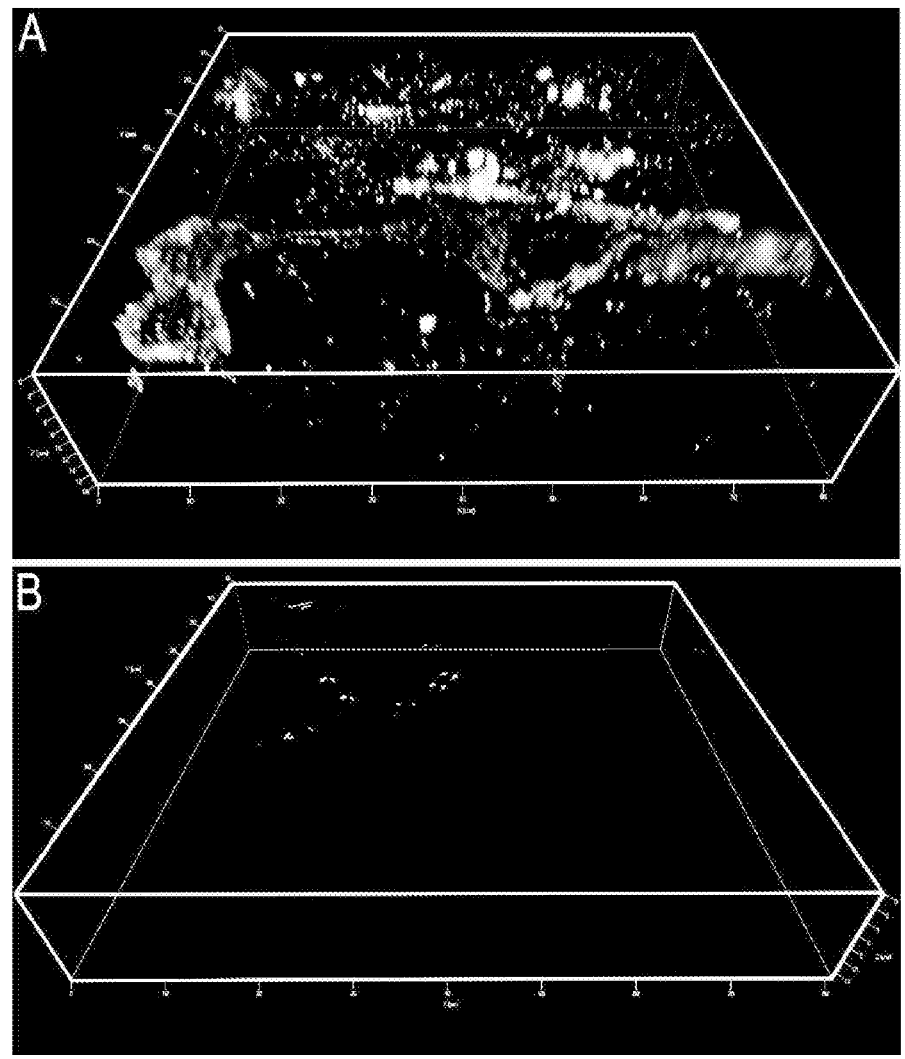
FIG. 4 Shows an immunofluorescence analysis of liver cells. Liver slices from qq and QQ Atlantic salmon (non-resistant and resistant, respectively, based on analysis using the DNA polymorphism corresponding to position 1065 within GenBank sequence BT058864.1 (BT058864.1_1065-TC)) were cultured and infected with IPNV in vitro. Visualization of IPN virions was carried out using immunofluorescence with a polyclonal rabbit antibody specific to IPNV. Positive signals appear as white spots or aggregates in heavily infected cells. A) Non-resistant fish (qq) show a widespread infection with virions on the surface cells as well as in hepatocytes located inside the tissue slice. B) In resistant animals, only a few IPNV particles trapped on the surface of the slice are visible.

To test IPNV infection in vitro, resistant and susceptible salmon (identified as such by the methods of the present invention) were sacrificed and liver biopsies were embedded in 2.5% ultra-low melt agarose dissolved in Hanks buffer. Liver sections of 250 mm were prepared in ice cold Hanks buffer using a vibratome (Compressotome VF300, Precisionary Instruments, USA) and transferred to L15 Glutamax with 1% PenStrep (Life Technologies, USA). After 24 hours in culture at 15° C., 90% of the surface cells and all cells within the tissue were viable, respectively. The organotypic liver cultures were challenged with IPNV and incubated overnight, washed in ice cold Hanks buffer and then fixated using freeze substitution at −100° C. Briefly, the section were frozen in isobutanol at −100° C. for 3 minutes and then transferred to pure ethanol, also at −100° C. The sections were slowly brought to room temperature after at least 3 days at −80° C. Immunofluorescence was carried out using antibodies against IPNV (1), Cdh1 (Dako, Denmark) and Clathrin (Abcam, United Kingdom). Briefly, the sections were rehydrated and blocked with 4% dry milk in PBS with 0.4% saponin (PBSS). After overnight incubation with primary antibodies diluted in PBSS, Alexa conjugated secondary antibodies (Life Technologies) were applied for 2 hours after extensive washing. The sections were mounted with 2,2'-thiodiethanol after washing with PBSS and examined at a fluorescence microscope (Zeiss Axio Observer, Carl Zeiss Microimaging GmbH, Germany). Images of sections from susceptible fish showed a widespread IPNV infection (see FIG. 4). The virus were located throughout the tissue slice and showed intracellular presence. On the surface of the hepatocytes, IPNV co-localized with cdh1 and clathrin in early clathrin coated pits forming early endsomes. These findings imply that IPNV enters cells through binding to cdh1 and subsequent entry depend upon clathrin mediated endocytosis. Analysis of liver section from resistant fish showed presence of only a few virus and only on the surface of the section. These virus are presumably trapped by cellular debris. IPNV were never detected within the tissue and no co-localization was observed between IPNV and cdh1 or clathrin.

7. PANCREAS DISEASE STUDY 7.1 Introduction Pancreas Disease

Pancreas disease (PD) is a viral fish disease with significant impact on salmon aquaculture in Norway, Scotland and Ireland. The disease is caused by a member of the Togaviridae family, an alphavirus, named salmonid alphavirus (SAV). Some strains of the virus are causing a related disease (sleeping disease) in farmed rainbow trout in several European countries. Outbreaks of PD can occur at all stages of the marine production cycle of Atlantic salmon (McLoughlin & Graham, 2007), and mortality rates can range from 0% up to 50% mortality. Clinical signs are characterized by sudden loss of appetite, lethargy, the appearance of fecal casts in the net pen and an increase in the mortality. A significant share of survivors will fail to grow and become runts. Histopatological examination of fish suffering from PD shows pancreatic necrosis, myocardial degeneration as well as inflammation of the heart and skeletal muscle. Vaccination has proven to give some, but not full, protection from the disease.

Figure 5:
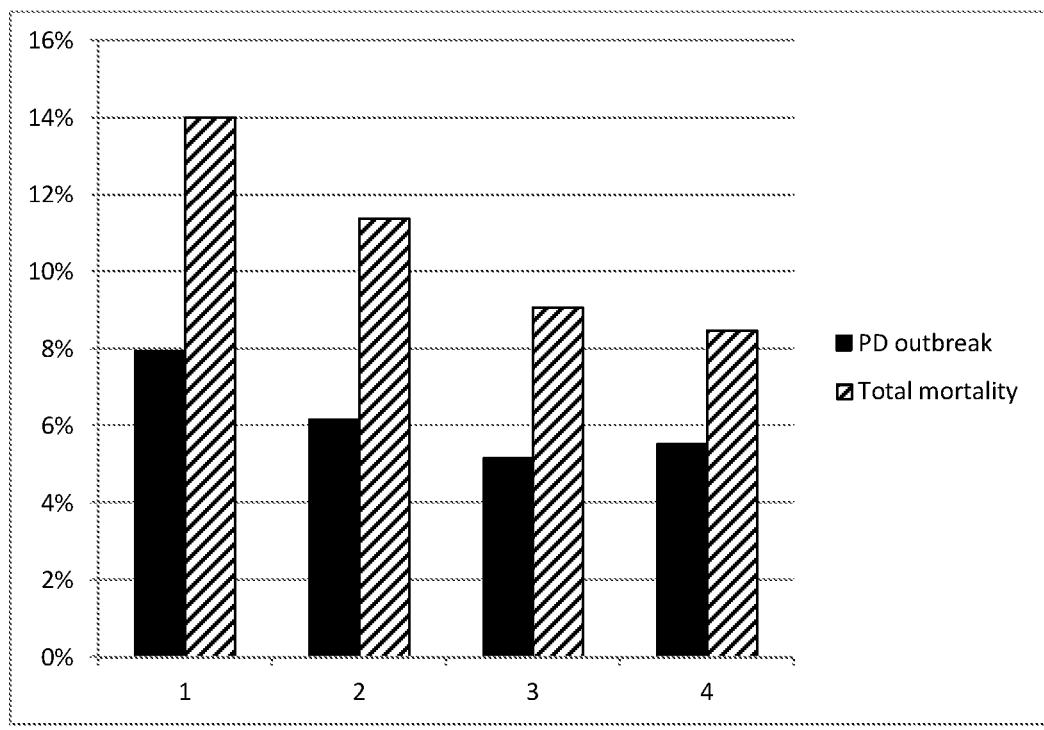
FIG. 5 shows mortality of AquaGen Atlantic salmon families from the 2005 year class related to an outbreak of pancreas disease at a sea site in western Norway. The families are ranked according to their breeding values for IPN resistance. 1: low, 2: medium to low, 3: medium to high or 4: high breeding values for IPN resistance.
Figure 6:
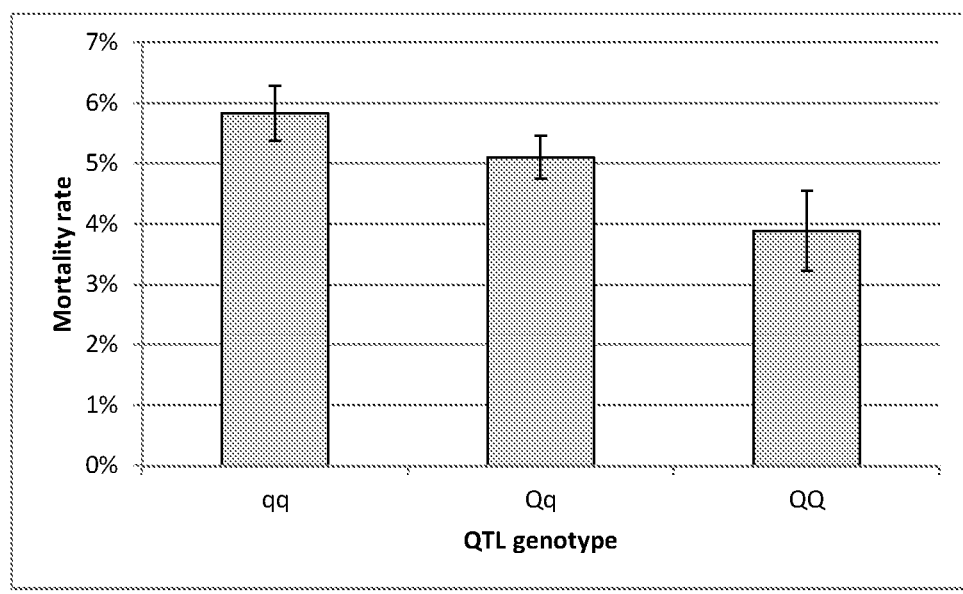
FIG. 6 shows mean rate of mortalities from pancreas disease within offspring of individual parents, categorized according to parental genotypes for IPN resistance qq=no copies of the resistance allele at BT058864.1_1065-TC, Qq=one copy of the resistance allele at BT058864.1_1065-TC, QQ=two copies of the resistance allele at BT058864.1_1065-TC.

7.2 Field Study 21725 fish from 394 families were transferred to a sea site on the west coast of Norway in May 2006, in a region where the SAV-3 variant of the PD virus is known to have an endemic distribution. The families originated from approximately 400 parents, each male having been mated to two dams and vice versa. The families were ranked according to their breeding value for IPN resistance based on the results in a previous IPN challenge study, as having: 1: low, 2: medium to low, 3: medium to high or 4: high breeding values for IPN resistance. An outbreak of pancreas disease started from April 2007, resulting in the total loss of 13.6% of the fish at the site. The total mortality of the population as well as the PD specific mortalities was lowest in the families of high or medium to high IPN resistance (FIG. 5). Tissue samples were harvested from approximately 50% of the mortalities. Individual samples were assigned to parental pairs using a panel of 9 microsatellite markers, 936 animals being successfully assigned to a parental pair. The within-family mortality rate ranged from 0% to 36%. Animals with two copies of the high-resistance allele (QQ) for BT058864.1_1065-TC appeared to be more resistant to PD than animals carrying one or two copies of the low-resistance allele (Qq or qq (p-value=0.12) (FIG. 6).

8. CHALLENGE STUDY TO TEST THE PROTECTION OF THE IPN QTL MARKERS AGAINST PANCREAS DISEASE

Figure 7:
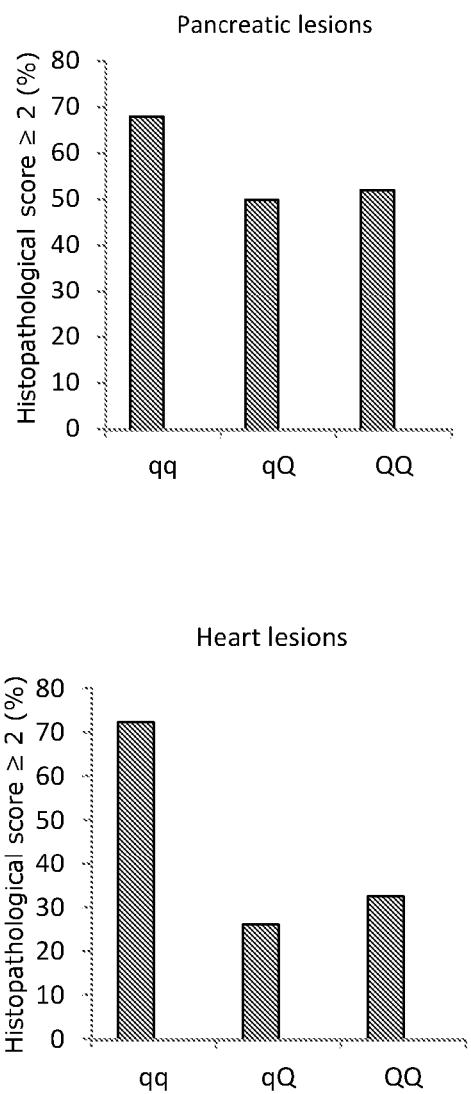
FIG. 7 shows histopathological scores of heart muscle and exocrine pancreas of fish of differing genotype to the IPN QTL 28 days after challenge with PD virus (SAV-3 variant).

During October 2011, broodfish previously genotyped for the IPN QTL genotype markers were selected as parents for a batch of test fish (ie using the IPN resistance marker BT058864.1_1065-TC). 6 females of the qq genotype and 4 females of the QQ genotype were used along with 4 males of the qq genotype and 6 males of the QQ genotype. 100 crosses among this fish were made, resulting in batches of offspring carrying the qq, Qq or QQ genotypes. Only offspring of the qq and QQ genotypes were used for a pancreas disease challenge study. The fish were reared in the freshwater hatchery of AquaGen Kyrksterøra Norway, pit-tagged and vaccinated using a commercial vaccine containing only bacterial antigens before transport to the VESO Vikan reseach station at approximately 75 grams. The challenge was performed in freshwater at 15° C. 60 fish of each genotype was kept in the same tank, along with 20% shedder fish previously injected with a Norwegian SAV-3 isolate of the PD virus. 12 fish from each genotype were sampled 18 days post challenge, and a PD-infection was confirmed by real-time RT-PCR detection of the SAV-3 virus in the hearts of fish of all of the three genotype categories. At 28 days post challenge, the heart, pancreas and muscle (red and white muscle) was sampled from the remaining fish in the tank (48 fish in each group of fish) for examination by histopathology. There was no mortality from PD during the challenge period. Samples were blinded and prepared, examined and scored for histopathology by Aquatic Veterinary Services, Belfast, Ireland, using a semi-quantitative scoring system ranging from 0 to 4 depending on the severity of the lesions. A statistical examination was performed on the results, demonstrating a significantly lower frequency of heart lesions in fish of the Qq and QQ genotypes. There was also a tendency toward lower frequency of pancreas and muscle lesions in the Qq and QQ fish (FIG. 7). Thus, it was confirmed that fish carrying the IPN-QTL demonstrate a higher resistance also to the PD-virus.

9. VIRAL/CADHERIN BINDING STUDY

Figure 8:
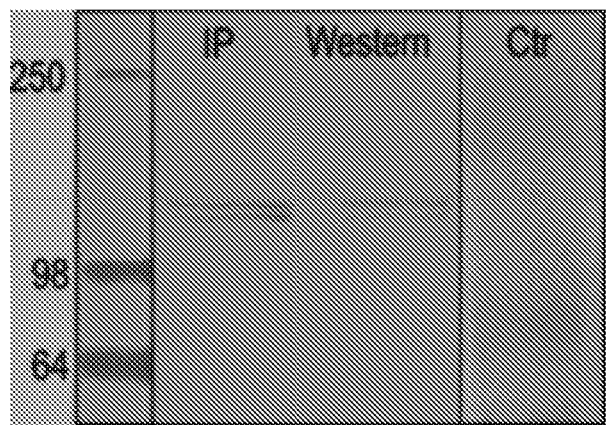
FIG. 8 shows results of a co-immunoprecipitation study (Co-IP) that verify direct binding of Cdh1-1 to IPNV.

CO-immunoprecipitation was carried out using an IPNV specific polyclonal antibody bound to Protein A coated magnetic beads. Briefly, a protein lysate was prepared from a salmon liver and mixed with IPNV for 30 min, before adding the coated magnetic beads and incubation for 30 min. After selective extraction of protein-IPNV bound to the magnetic beads, the eluate was subjected to a SDS-PAGE gel electrophoresis together with a liver protein lysate (positive Cdh1-1 control) and a negative control co-immunoprecipitation reaction without IPNV. After gel separation the proteins were transferred to a membrane and Cdh1-1 immunoprecipitated by IPNV was detected using a specific antibody for Cdh1-1. The presence of Cdh1-1 in the gel clearly demonstrates that IPNV binds to the Cdh1-1 protein. See the results in FIG. 8.

REFERENCES

Granzow H. Weiland F. Fichtner D and Enzmann P J (1997) *Studies of the ultrastructure and morphogenesis of fish pathogenic viruses grown in cell culture. Journal of Fish Diseases* 20: 1-10

Falk K, Namork E, Dannevig B H (1998) Characterization and applications of a monoclonal antibody against infectious salmon anaemia virus. Dis Aquat Organ 8: 77-85.

Houston R D, Haley C S, Hamilton A, Guy D R, Tinch A E, Taggart J B, McAndrew B J, Bishop S C (2008) Major quantitative trait loci affect resistance to infectious pancreatic necrosis in Atlantic salmon (*Salmo salar*). Genetics 178: 1109-15.

Houston R D, Davey J W, Bishop S C, Lowe, N R, Mota-Velasco J C et al. (2012) Characterisation of QTL-linked and genome-wide restriction site-associated DNA (RAD) markers in farmed Atlantic salmon. BMC Genomics 13: 244.

Kuznar J, Soller M, Fabias G, Espinoza J C (1995) Attachment and entry of infectious pancreatic necrosis virus (IPNV) into CHSE-214 cells. Arch Virol 140: 1833-40.

Lien S, Gidskehaug L, Moen T, Hayes B J, Berg P R, Davidson W S, Omholt S W, Kent M P (2011) A dense SNP-based linkage map for Atlantic salmon (*Salmo salar*) reveals extended chromosome homeologies and striking differences in sex-specific recombination patterns. BMC Genomics 12: 615.

Madsen and Jensen (2008) DMU: a user's guide. A package for analysing multivariate mixed models, version 6, release 5.0. University of Aarhus, Tjele, Denmark.

McLoughlin M F, Graham D A (2007). Alphavirus infections in salmonids—a review. J. Fish Dis. 30: 511-531.

Moen T, Hayes B, Baranski M, Berg P R, Kjøglum S, Koop B F, Davidson W S, Omholt S W, Lien S (2008) A linkage map of the Atlantic salmon (*Salmo salar*) based on EST-derived SNP markers. BMC Genomics 9: 223.

Moen T, Baranski M, Sonesson A K, Kjøglum S (2009) Confirmation and fine-mapping of a major QTL for resistance to infectious pancreatic necrosis in Atlantic salmon (*Salmo salar*): population-level associations between markers and trait. BMC Genomics 10: 368.

Palacious G, Lovoll M, Tengs T, Hornig M, Hutchison S et al. (2010) Heart and Skeletal Muscle Inflammation of Farmed Salmon is Associated with Infection with a Novel Reovirus. PLoS ONE 5: e11487

Shifman S, Kuypers J, Kokoris M, Yakir B, Darvasi A (2003) Linkage diseuilibrium patterns of the human genome across populations. Human Molecular Genetics 12: 771-776.

Thorsen J, Zhu B, Frengen E, Osoegawa K, de Jong, P J, Koop B F, Davidson W S, Høyheim B (2005) A highly redundant BAC library of Atlantic salmon (*Salmo salar*): an important tool for salmon projects. BMC Genomics 6: 50.

Yoon M, Spear P G (2002). Disruption of adherens junctions liberates nectin-1 to serve as receptor for herpes simplex virus and pseudorabies virus entry. *J Virol.* 76:7203-8.

The invention claimed is:

1. A method of detecting at least one variant in a cadherin protein Cdh1 and/or at least one allele present in a DNA polymorphism in the gene for cadherin cdh1 comprising:
   a) obtaining a sample from an Atlantic salmon;
   b) assaying the sample for a variant in the Cdh1 protein or an allele of a DNA polymorphism in the cdh1 gene; and
   c) detecting the presence of a proline at amino acid position 325 of the Cdh1-1 protein or a cytosine at nucleotide position 1065 in SEQ ID NO. 12.

2. A method of breeding Atlantic salmon, the method comprising:
   breeding from an Atlantic salmon, wherein the Atlantic salmon has a proline at position 325 in the amino acid sequence for the cadherin protein Cdh1-1; and
   wherein a sample from the Atlantic salmon has been tested to detect the presence of a proline at amino acid position 325 of the Cdh1-1 protein.

3. A method of breeding Atlantic salmon, the method comprising:
   breeding from an Atlantic salmon, wherein the Atlantic salmon has a cytosine variant at position 1065 in SEQ ID NO. 12, the DNA sequence for the cadherin gene cdh1; and
   wherein a sample from the Atlantic salmon has been tested to detect the presence of a cytosine at nucleotide position 1065 in SEQ ID NO. 12.

4. The method of claim 1, wherein the method further comprises breeding from the salmon.

* * * * *

```
                     SEQUENCE LISTING

<160> NUMBER OF SEQ ID NOS: 12

<210> SEQ ID NO 1
<211> LENGTH: 41
<212> TYPE: DNA
<213> ORGANISM: Salmo salar

<400> SEQUENCE: 1
ccaacatgtt tgtcatcaac cctgtgactg gagggattcg g                 41

<210> SEQ ID NO 2
<211> LENGTH: 41
<212> TYPE: DNA
<213> ORGANISM: Salmo salar

<400> SEQUENCE: 2
ccaacatgtt tgtcatcaac tctgtgactg gagggattcg g                 41

<210> SEQ ID NO 3
<211> LENGTH: 40
<212> TYPE: DNA
<213> ORGANISM: Salmo salar

<400> SEQUENCE: 3
tatcgaagtt ctttttttt tatatgacta tcctttggca                    40

<210> SEQ ID NO 4
<211> LENGTH: 41
<212> TYPE: DNA
<213> ORGANISM: Salmo salar

<400> SEQUENCE: 4
tatcgaagtt ctttttttt atatatgact atcctttggc a                  41

<210> SEQ ID NO 5
<211> LENGTH: 40
```

```
<212> TYPE: DNA
<213> ORGANISM: Salmo salar

<400> SEQUENCE: 5
ggactttgag cacgtgtttt gacggtgtag gaagtttttg                    40

<210> SEQ ID NO 6
<211> LENGTH: 42
<212> TYPE: DNA
<213> ORGANISM: Salmo salar

<400> SEQUENCE: 6
ggactttgag cacgtgtttt atgacggtgt aggaagtttt tg                 42

<210> SEQ ID NO 7
<211> LENGTH: 41
<212> TYPE: DNA
<213> ORGANISM: Salmo salar

<400> SEQUENCE: 7
gatgacacta aatcgcaggg gtgcgcctgc gtacgttatg a                  41

<210> SEQ ID NO 8
<211> LENGTH: 41
<212> TYPE: DNA
<213> ORGANISM: Salmo salar

<400> SEQUENCE: 8
gatgacacta aatcgcaggg atgcgcctgc gtacgttatg a                  41

<210> SEQ ID NO 9
<211> LENGTH: 30
<212> TYPE: DNA
<213> ORGANISM: Salmo salar

<400> SEQUENCE: 9
acgttggatg ctcactctgt ttaggtgacg                               30

<210> SEQ ID NO 10
<211> LENGTH: 30
<212> TYPE: DNA
<213> ORGANISM: Salmo salar

<400> SEQUENCE: 10
acgttggatg attaacccga atccctccag                               30

<210> SEQ ID NO 11
<211> LENGTH: 17
<212> TYPE: DNA
<213> ORGANISM: Salmo salar

<400> SEQUENCE: 11
gatccctcca gtcacag                                             17

<210> SEQ ID NO 12
<211> LENGTH: 3501
<212> TYPE: DNA
<213> ORGANISM: Salmo salar

<400> SEQUENCE: 12
acacgtttga aaatagact tttctcatct acacgtaaag ggattacttg ttactattgg    60
tggaacgact atccaaaaat tattcaaaac aaatggggc attttggttc gtggagttgg   120
```

```
gcgtattaat attatttctc caggctttca aaccagggtc gtcggagtca acatgtctac    180
caggttttcaa ttcagaaata tacattttca aagtggaaag aaatcactta caaagtggcc   240
ggagactagg aaaagtggtt tttgatgact gcaccagccg caccagcttt ctctttcact    300
ccgaggattc acacttcaaa gtagatggcg acgggacgct gaaactggag aggggggctga   360
ctctgcataa tggacataag gaggtctatg tctctaccca gtccaagggc aagaagatca    420
cggttccagt cagagtgctg catgaggcca gacatggcca ccaccacaat caccatgaga    480
tgaccaccca gcccaagcca ggagcaagtc tgtctctacc tgttctgaac ttccccaagt    540
cttcaggagg tctgaaaaga aggaagaggg actgggtcat tcctcccatc aacttcccag    600
agaatgaccg aggccccttc cccaagatta tggtgcagat caggtccaac aatgataaag    660
aggtgaagat ccagtacagc atcactggca ctggggcaga cctacctcct gtgggaatct    720
tcactgtgga caaaaactct gggaatctct atgtgaccga gcccttggac agggagaaaa    780
aagacaaata cattctccta gcccatgctg ttgcagtggg tgcaggtata gctgaggatc    840
ccatggagat cattgtgaaa gtcatcgata tgaatgacaa caaacctgta tttacccaag    900
atccatttat gggaacagtt cctgaagcat caaaaccagg tgacgaggtc atgcaggtaa    960
cggccactga tgctgatgag gagggctctg ccaattctga tgtcagatac accattctca   1020
gtcaggagcc tccactacca agccccaaca tgtttgtcat caactctgtg actggaggga   1080
ttcgggttaa tgcacctggg ttggacagag agaaaattcc caatatact ttggcaatcc    1140
aagctgccga tatggaggga aatggcctta ccagctttgg caaagccatc attacactaa   1200
cggacagcaa tgacaacgcg ccacagtttt gacgccttc gtacaccgtg tcagtcccag    1260
agaataaagt ggatgccttg gtggtgaaaa tgccagtgac tgatggagat gagcctcact   1320
cctctgcctg ggccaccacc tacaagatag ttgacgggga ccctcaaggc cttttcaacg   1380
tgagcacagg ccctagcaag ctggagggca tcattacaac agccaagccg cttgactttg   1440
agaagaacaa caagtacact ctgctggtca ctgtgcagaa tgaagtccca ttcacaatca   1500
gcatgcccac ctccactgct actgttgtag tgaatgtgga ggatgtgaat gaagctccag   1560
tcttcacccc agtggagaag attatcagga aacctgagga cctccctgtt gacagtgacc   1620
tggttctgta cacagccaca gacccagaca ccgcaaggaa tcagaaagtc acatacaaga   1680
tacgcaatga taatgctgga tggctcagta tcaacaaaga cactgggctg atcaaagtca   1740
agagcctcat ggacagagaa tccacttttg tccaagacaa caaatactct gttattgttc   1800
tgggcatcga caacgatgaa atcccggcaa ctggcactgg caccctaatc atagagctgg   1860
aggatgtgaa tgataatgct ccaaccattg acgagagtgt gatcagggtc tgcaacaagg   1920
agtcctcccc acagttgttg tcagtcactg ataaagatgg tgcgggcttc actgctccat   1980
acaccgtaca gcttcagggg tcgtcccatt ctaactggac tgccagaatg aacgacacaa   2040
agactggcat tatcctgact ctgaagacta tgttggacag tggagattac acggttgtcc   2100
tgagagtgtc tgacaaccag ggcctgcacc atgacagcac catccaggcc tccgtctgtg   2160
actgcaaagg agcggatgtc cagtgctccg ataaagctgt agcaggcttc ggcatctcta   2220
gcattctggg aattctagga gcagtcttac tactcctatt gttgtctctt ctgctgctca   2280
tgttcctgag gaagagaggt ggcgagaaga aggagcctct gctgcaggag gacgatgtca   2340
gggacaacat ctactactat gacgaggagg gaggtggcga ggatgaccag gatttcgact   2400
tgagcgttct gcagagagt ctggataacc gtcctgatgt tttccgtaat gacatcgctc    2460
caacatggc ccggccagag tatcgtccac gacccgccaa cccagccgac attggcaact    2520
```

```
tcattgatga taacctgaag gcagctgaca acgacccccac tgctcctccc tacgactccc  2580
tcctggtgtt tgactatgaa ggaggtggct ctgaggctgg ctccctcagt tccctcaact  2640
cctccagctc aggagacgac caggactacg acctccttca agagtggggc ccgcgcttca  2700
agaagctgtc tgacatgtac ggaggaggag aggattgaga agtcagtcag ccactaaacc  2760
tttttgcttg gaaactgtcc ggttctccac actttggtct gtaaactgaa gaccttttct  2820
ttatttcccc tttttatgcg tttcgggcac atttacagtt tggcaatttg atttgtgcag  2880
acatgggacc attttagaaa aaatgtgttc aatgctcgtc ttcagcatgg ggagggtggc  2940
atactcttgg ctctgcacta gcaggatgtt gacatggatt ttacacaatt cagcagttct  3000
ttctaatgga ctcttaacaa ccccagattg tacttgaatt taatatgctt cttttggcgt  3060
cgtatcgaag ttctttttt ttatatatga ctatcctttg gcatgaaatt gaagttactg  3120
aaagccaaat cagccttacg atgtttttgt taactgagat taattatcaa gctcaataaa  3180
tgcttttaaa aatgtttgat aaacaactaa gtttgggttg ttttattcct tttcatttta  3240
atcatattaa tcactaatta tatatttttt tcctgaagaa gctcacagtt ctgcttttta  3300
ttttattaca gttctgcttt tttaaattaa agatatcctt ttggtacaat gatggatgtg  3360
aatatttgta ttaaatacat tgtaatttgt cttatttga gctcaattat tcaaattcac  3420
agctgagaca ctagatggcg acaattgaat aaaacaggtc ttggtcaatg aaaaaaaaaa  3480
aaaaaaaaaa aaaaaaaag a                                             3501
```